United States Patent [19]
Kamiya et al.

[11] 3,984,397
[45] Oct. 5, 1976

[54] 2,3-LOWER ALKYLENEPENAM-3-CARBOXYLIC ACID DERIVATIVES AND PROCESSES FOR THE PREPARATION THEREOF

[75] Inventors: Takashi Kamiya, Suita; Tsutomu Teraji; Masashi Hashimoto, both of Toyonaka, all of Japan

[73] Assignee: Fujisawa Pharmaceutical Co., Ltd., Osaka, Japan

[22] Filed: June 13, 1975

[21] Appl. No.: 586,585

Related U.S. Application Data
[62] Division of Ser. No. 418,259, Nov. 23, 1973, Pat. No. 3,904,607.

[30] Foreign Application Priority Data
Nov. 22, 1972 Japan.............. 47-117385

[52] U.S. Cl. ................................ 260/239.1
[51] Int. Cl.² .............. C07D 499/44; C07D 499/46; C07D 499/50; C07D 499/58
[58] Field of Search ................... 260/239.1

[56] References Cited
UNITED STATES PATENTS
3,466,275  9/1969  Morin et al. .................... 260/239.1

*Primary Examiner*—Gerald A. Schwartz
*Attorney, Agent, or Firm*—Oblon, Fisher, Spivak, McClelland & Maier

[57] ABSTRACT

A process for the preparation of

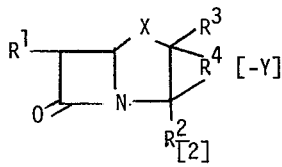

which comprises reacting

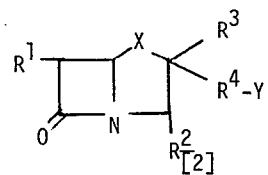

with a base, wherein Y is a residue of an acid, wherein $R^1$ is amino, (halophenylimino-1-lower alkanoylthiomethyl)amino or acylamino and wherein $R^2$ is carboxy or a protected carboxy, $R^3$ is lower alkyl, $R^4$ is lower alkylene and X is —S— or

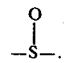

1 Claim, No Drawings

2,3-LOWER ALKYLENEPENAM-3-CARBOXYLIC ACID DERIVATIVES AND PROCESSES FOR THE PREPARATION THEREOF

This is a division of application Ser. No. 418,259, filed Nov. 23, 1973, now U.S. Pat. No. 3,904,607.

The present invention relates to 2,3-lower alkylenepenam-3-carboxylic acid derivatives. More particularly, it relates to a new 2,3-lower alkylenepenam-3-carboxylic acid derivatives which have antimicrobial activities and are useful as intermediates, to processes for the preparation thereof, to pharmaceutical composition comprising the same, and to a method of using the same therapeutically in the treatment of infections.

Accordingly, it is one object of this invention to provide the antimicrobially active 2,3-lower alkylenepenam-3-carboxylic acid derivatives, which are active against a number of microorganisms, especially gram positive, for example, Staphylococcus and Bacillus species, and are also useful as intermediates for preparing antimicrobially active 3-cephem-4-carboxylic acid derivatives.

Another object of the present invention is to provide processes for the preparation of 2,3-lower alkylenepenam-3-carboxylic acid derivatives by synthesis.

A further object of the invention is to provide pharmaceutical composition comprising, as effective antimicrobial agents, said 2,3-lower alkylenepenam-3-carboxylic acid derivatives and the salt thereof.

Still further object of the present invention is to provide a method of treating infections disease caused by bacteria in human and animals.

The 2,3-lower alkylenepenam-3-carboxylic acid derivatives are novel compound and comprise a new and unique nucleus in the chemical structure, which has been unexpected to the skilled in the arts, and can be represented by the following formula(I).

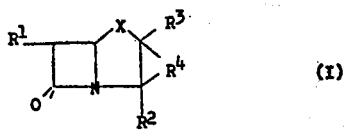

Wherein
R¹ is amino or a substituted amino,
R² is carboxy or a protected carboxy.
R³ is lower alkyl.
R⁴ is lower alkylene, and

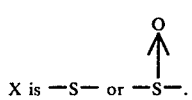

X is —S— or —S—.

According to the present invention, the 2,3-lower alkylenepenam-3-carboxylic acid derivatives can be prepared by various procedures, and the said processes are illustrated collectively for convenience's sake by the following scheme, in which the process comprising step, (II) ⟶ (I) is a fundamental process and the others are alternative processes.

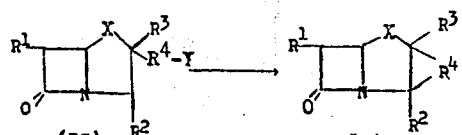
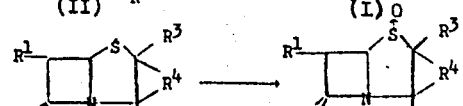
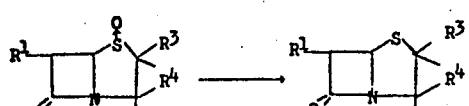
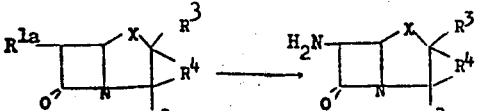
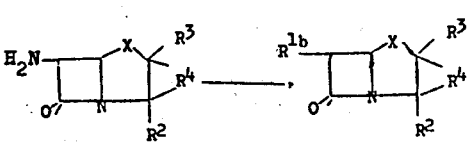
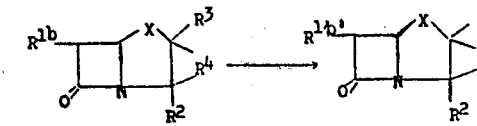
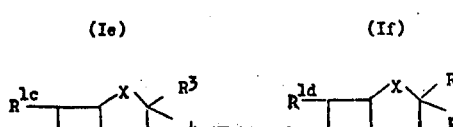
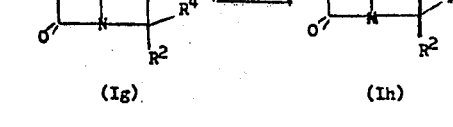
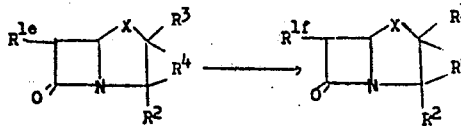
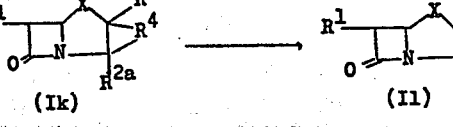
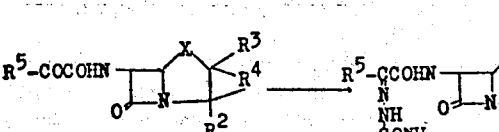

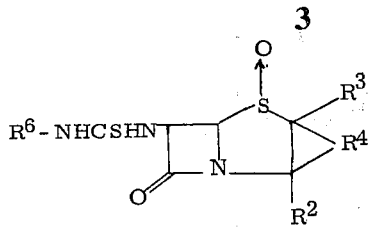

(Io)

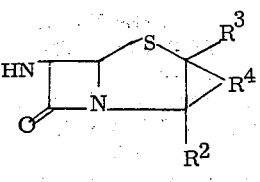

(Ip)

wherein R¹ is amino or a substituted amino,
R² is carboxy or a protected carboxy,
R³ is lower alkyl, R⁴ is lower alkylene,
R⁵ and R⁶ are each aryl or a substituted aryl,
R⁷ is acyl,

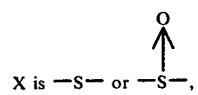

Y is a residue of an acid,
$R^{1a}$ is a protected amino,
$R^{1b}$ and $R^{1b}$ are each acylamino,
$R^{1c}$ is acylamino having a protected amino,
$R^{1d}$ is acylamino having an amino,
$R^{1e}$ is acylamino having a protected hydroxy,
$R^{1f}$ is acylamino having a hydroxy, and
$R^{2a}$ is a protected carboxy.

Among the starting compounds (II), methyl 2-acetoxymethyl-2-methyl-6-(2-phenoxyacetamido)penam-3-carboxylate and benzyl 2-acetoxymethyl-2-methyl-6-(2-phenoxyacetamido)penam-3-carboxylate can be prepared according to the method described in U.S. Pat. No. 3,466,275 and the other starting compounds (II) can be prepared be reacting the corresponding 2-oxo-3-amino (or a substituted amino)-4-substituted amino (or substituted thio)-substituted thio-1-azetidine-α-(1-alkylvinyl)acetic acid or its derivative at the carboxy with the corresponding condensating agent capable for introducing a residue of an acid such as hydrogen chloride.

In the above and subsequent description, the term "a substituted amino" in R¹ means suitable substituted amino groups which may include hydrazino, mono(or di)-(lower)alkylamino, mono(or di)-(lower) alkenylamino, lower alkylideneamino, ar(lower)alkylideneamino, 1-substituted or unsubstituted arylimino-1-acylthiomethylamimo, acylamino and amino group substituted by other amino protecting groups than the acyl groups.

In the above suitable substituted amino group, suitable lower alkyl moiety in the mono(or di)-lower alkylamino may include methyl, ethyl, propyl, isopropyl, butyl, etc.; suitable lower alkenyl moiety in the mono(or di)-(lower)-alkenylamino may include allyl, 2-butenyl, etc.; suitable lower alkylidene moiety in the lower alkylideneamino may include ethylidene, propylidene, butylidene, etc.; suitable ar(lower)alkylidene moiety in the ar(lower)-alkylidene may include benzylidene, phenethylidene, etc.;

suitable acyl moiety in the acylamino groups may include carbamoyl, aliphatic acyl groups and acyl groups containing an aromatic or heterocyclic ring, examples of which are illustrated below.

That is, suitable aliphatic acyl groups may include saturated or unsaturated lower or higher alkanoyl groups which may be branched or which may contain a cyclic ring; such as lower or higher aliphatic acyl groups, for example, lower alkanoyl (e.g., formyl, acetyl, propionyl, butyryl, isobutyryl, valeryl, isovaleryl, oxalyl, succinyl, pivaloyl, etc.), higher alkanoyl (e.g., octanoyl, lauroyl, palmitoyl, etc.), lower alkenoyl (e.g., acryloyl, crotonoyl, etc.), lower alkynoyl(e.g., propynoyl, etc.), lower or higher cycloalkanecarbonyl (e.g., cyclopentanecarbonyl, cyclohexanecarbonyl, cycloheptanecarbonyl, etc.), lower or higher cycloalkyl(-lower)alkanoyl(e.g., cyclopentylacetyl, cyclohexylacetyl, cycloheptylacetyl, cyclohexylpropionyl, cycloheptylpropionyl, etc.), lower or higher cycloalkadiene carbonyl(e.g., dihydrobenzoyl, etc.), lower or higher cycloalkadienyl(lower)alkanoyl (e.g., dihydrophenylacetyl, dihydrophenylpropionyl, etc.), etc.; and lower or higher aliphatic acyl groups containing a oxygen or sulfur atom, for example, lower alkoxy(lower)alkanoyl (e.g., methoxyacetyl, ethoxyacetyl, methoxypropionyl, etc.), lower alkylthio(lower)alkanoyl (e.g., methylthioacetyl, ethylthioacetyl, methylthiopropionyl, etc.), lower alkenylthio(lower)alkanoyl(e.g., allylthioacetyl, allylthiopropionyl, etc.), lower or higher cycloalkylthio(lower)alkanoyl(e.g., cyclopentylthioacetyl, cyclohexylthiopropionyl, cycloheptylthioacetyl, etc.), lower or higher cycloalkoxy(lower)alkanoyl(e.g., cyclopentyloxyacetyl, cyclohexyloxypropionyl, etc.), lower or higher cycloalkanedienyloxy(lower) alkanoyl-(e.g., dihydrophenoxyacetyl, dihydrophenoxypropionyl, etc.), lower or higher cycloalkanedienylthio(-lower)alkanoyl(e.g., dihydrophenylthioacetyl, dihydrophenylthiopropionyl, etc.), lower alkoxycarbonyl (e.g., methoxycarbonyl, ethoxycarbonyl, propoxycarbonyl, 1-cyclopropylethoxycarbonyl, isopropoxycarbonyl butoxycarbonyl, tertiarybutoxycarbonyl, etc.), lower or higher cycloalkyloxycarbonyl (e.g., cyclopentyloxycarbonyl, cyclohexyloxycarbonyl, cycloheptyloxycarbonyl, etc.), lower or higher cycloalkanedienyloxycarbonyl (e.g., dihydrophenoxycarbonyl, etc.), etc.

Suitable acyl groups containing an aromatic ring such as benzene, naphthalene and the like may include, for example, arylcarbamoyl (e.g., phenylcarbamoyl, etc.), aryloyl (e.g., benzoyl, toluoyl, naphthoyl, δ-methylnaphthoyl, phthaloyl, benzenesulfonyl, tetrahydronaphthoyl, indancarbonyl, etc.), ar(lower)alkanoyl (e.g., phenylacetyl, phenylpropionyl, phenylbutyryl, tolylacetyl, xylylacetyl, naphthylacetyl, tetrahydronaphthylacetyl, indanylacetyl, etc.), and the carbon atom in the alkyl moiety of said ar(lower)alkanoyl group may be replaced by an oxygen or sulfur atom or carbonyl group, example of which are aryloxy(lower)alkanoyl(e.g., phenoxyacetyl, phenoxypropionyl, phenoxybutyryl, xylyloxyacetyl, etc.), aryloxycarbonyl (e.g., phenoxycarbonyl, xylyloxycarbonyl, naphthyloxycarbonyl, indanyloxycarbonyl, etc.), ar(lower)alkoxycarbonyl (e.g., benzyloxycarbonyl, phenethyloxycarbonyl, etc.), arylthio(lower) alkanoyl(e.g., phenylthioacetyl, phenylchiopropionyl, etc.), arylglyoxyloyl (e.g., phenylglyoxyloyl, etc.), etc.

Suitable acyl groups containing an heterocyclic ring may include heterocyclic carbonyl or heterocyclic lower alkanoyl; and the heterocyclic ring in the heterocyclic carbonyl or heterocyclic lower alkanoyl may be saturated or unsaturated, monocyclic or polycyclic and may contain at least one hetero-atom, such as an oxygen, sulfur, nitrogen atom or the like, examples of which are illustrated by unsaturated 3 to 8-membered heteromonocyclic containing a sulphur atom(e.g., thenyl, etc.), unsaturated condensed-heterocyclic containing a sulfur atom(e.g., benzothienyl, etc.), unsaturated 3 to 8-membered heteromonocyclic containing an oxygen atom(e.g., furyl, 2(or 4)pyranyl, 5,6-dihydro-2H-pyran-3-yl,etc.), unsaturated 3 to 8-membered heteromonocyclic containing 1 to 4 nitrogen atom(s) (e.g., pyrrolyl, 2(or 3)H-pyrrolyl, 2(or 3)-pyrrolinyl, imidazolyl, pyrazolyl, pyridyl, pyrimidyl, pyrazinyl, pyridazinyl, 1H-tetrazolyl, 2H-tetrazolyl, etc.), saturated 3 to 8-membered heteromonocyclic containing 1 to 2 nitrogen atom(s) (e.g., pyrrolidinyl, imidazolidinyl, piperidino, piperadinyl, etc.), unsaturated condensed-heterocyclic containing 1 to 3 nitrogen atom(s) (e.g., indolyl, isoindolyl, indolizinyl, benzimidazolyl, quinolyl, isoquinolyl, 1(or 2)H-indazolyl, 1(or 2)H-benzotriazolyl, etc.), unsaturated 3 to 8-membered heteromonocyclic containing an oxygen atom(s) and 1 to 3 nitrogen atom(s)(e.g., oxazolyl, isoxazolyl, oxadiazolyl, etc.), saturated 3 to 8 membered heteromonocyclic containing 1 to 2 oxygen atom(s) and 1 to 2 nitrogen atom(s) (e.g., sydnonyl, etc.), unsaturated 3 to 8-membered heteromonocyclic containing a sulfur atom and 1 to 3 nitrogen atom(s) (e.g., thiazolyl, thiadiazolyl, etc.), unsaturated condensed-heterocyclic containing an oxygen atom and 1 to 2 nitrogen atom(s) (e.g., benzoxazolyl, benzoxadiazolyl, etc.) and unsaturated condensed-heterocyclic containing a sulfur atom and 1 to 2 nitrogen atom(s) (e.g., benzothiazolyl, benzothiadiazolyl, etc.), etc. And, the carbon atom in the lower alkyl moiety in said heterocyclic lower alkanoyl as mentioned above may be replaced by an oxygen or sulfur atom examples of which are heterocyclic lower alkoxycarbonyl, heterocyclic-oxycarbonyl, heterocyclic-oxy(lower)alkanoyl and heterocyclic-thio(lower)-alkanoyl.

Further, the carbamoyl, the aliphatic acyl groups and the acyl groups containing an aromatic or heterocyclic ring as mentioned above may have 1 to 10 appropriate substituent(s) such as lower alkyl (e.g., methyl, ethyl, propyl, isopropyl, etc.), lower alkenyl (e.g., 1-propenyl, allyl, etc.), lower or higher cycloalkyl (e.g., cyclopropyl, cyclopentyl, cyclohexyl, cycloheptyl, etc.), lower alkoxy (e.g., methoxy, ethoxy, propoxy, isopropoxy, etc.), lower alkylthio(e.g., methylthio, ethylthio, etc.), aryl(e.g., phenyl, xylyl, tolyl, indanyl, etc.), ar(lower)alkyl(e.g., benzyl, phenethyl, etc.), halogen (e.g., chlorine, bromine, fluorine, etc.), halophenyl (e.g., chlorophenyl, bromophenyl, etc.), halophenoxy(e.g., chlorophenoxy, bromophenoxy, etc.), cyano, lower alkylsulfinyl (e.g., methylsulfinyl, ethylsulfinyl, etc.), lower alkanesulfonyl (e.g., methanesulfonyl, ethanesulfonyl, etc.), lower alkoxycarbonyl(lower) alkoxy (e.g., methoxycarbonylmethoxy, ethoxycarbonylethoxy, 1-cyclopropylethoxycarbonylmethoxy, tertiarybutoxycarbonylmethoxy, etc.), nitro, sulfo, amino, azido, mercapto, carboxy, hydroxy, hydroxyamino, mono(or di)alkylamino (e.g., mono(or di)methylamino, mono(or di)ethylamino, mono(or di)propylamino, mono(or di)isopropylamino, etc..

When the acyl group as mentioned above may have a functional group, such as amino, hydroxy, mercapto, carboxy, etc., and the functional groups may also be protected by an appropriate protective group. Suitable protective group for the amino group may include any of the conventional protective groups, for example, the acyl groups or other groups than the acyl groups such as trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxo-cyclohexylidene(among these, 1-methoxycarbonyl-2-propylidene and 2-ethoxycarbonylcyclohexylidene radicals may be representable as 1-methoxycarbonyl-1-propene-2-yl and 2-ethoxycarbonyl-1-cyclohexenyl radical, respectively), mono or disilyl, etc.;

suitable protective groups for hydroxy or mercapto groups may include any of the conventional protective groups for hydroxy or mercapto groups, for example, the acyl groups or other groups than the acyl group such as benzyl, trityl, methoxymethyl, 2-nitrophenylthio, 2,4-dinitrophenylthio, etc.; and suitable protective groups for the carboxy group may include any of those conventional protective groups used for protecting a carboxy group, for example, lower alkyl ester (e.g., methyl ester, ethyl ester, propyl ester, butyl ester, 1-cyclopropylethyl ester, tertiarybutyl ester, etc.), mono(or di or tri)halo(lower)alkyl ester (e.g., chloromethyl ester, 2,2,2-trichloroethyl ester, 3,3-dibromopropyl ester, etc.), aryl ester (e.g., phenyl ester, nitrophenyl ester, indanyl ester, etc.), ar(lower)alkyl ester (e.g., benzyl ester, diphenylmethyl ester, triphenylmethyl ester, p-nitrobenzyl ester, p-bromobenzyl ester, etc.), tri(lower)alkylsilyl ester (e.g., trimethylsilyl ester, triethylsilyl ester, etc.) etc.

Further, as the amino protective group other than an acyl group which is mentioned in the above paragraph for explanation of the term "a substituted amino", there may be also illustrated the same amino protective groups as those which are exemplified as the protective groups for the amino radical in the acyl group as mentioned above.

Particularly suitable examples of the acyl groups may be illustrated as follows:

1. lower alkoxycarbonyl(e.g., methoxycarbonyl, ethoxycarbonyl, propoxycarbonyl, 1-cyclopropylethoxycarbonyl, butoxycarbonyl, tertiarybutoxycarbonyl, etc.),
2. lower alkylthio(lower)alkanoyl (e.g., 2-methylthioacetyl, 2-methylthiobutyryl, 2-ethylthioacetyl, 3-methylthiopropionyl, etc.),
3. lower alkenylthio(lower)alkanoyl (e.g., 2-allylthioacetyl, 3-allylthiopropionyl, etc.)
4. cyano(lower)alkanoyl (e.g., 2-cyanoacetyl, 3-cyanopropionyl, 4-cyanobutyryl, etc.),
5. phenyl(lower)alkanoyl (e.g., 2-phenylacetyl, 3-phenylpropionyl, 4-phenylbutyryl, etc.),
6. phenoxy(lower)alkanoyl (e.g., 2-phenoxyacetyl, 3-phenoxypropionyl, 4-phenoxybutyryl, etc.),
7. phenylcarbamoyl,
8. phenylglyoxyloyl,
9. phenylthiocarbonyl,
10. phenyl and amino substituted lower alkanoyl (e.g., phenylglycyl, 3-amino-3-phenylpropionyl, etc.),
11. phenyl and hydroxy substituted lower alkanoyl (e.g., 2-hydroxy-2-phenylacetyl, 2-hydroxy-3-phenylpropionyl, etc.), 12. phenyl and lower alkoxycarbonylamino substituted lower alkanoyl (e.g., N-methoxycarbonylphenylglycyl, N-ethoxycarbonylphenylglycyl, N-(1-cyclopropylethoxy)-carbonyl-phenylglycyl, N-tertiarybutoxycarbonylphenylglycyl, 2-(1-cyclopropylethoxy)carbonylamino-3-phenylpropionyl, etc.), 13. phenyl and trihalo(lower)alkoxycarbonylamino substituted lower alkanoyl (e.g., N-trichloroethoxycarbonylphenylglycyl, 3-trichloroethoxycarbonylamino-3-phenylpropionyl, N-tribromoethoxycarbonylphenylglycyl, etc.), 14. phenyl and lower alkanoyloxy substituted lower alkanoyl (e.g., 2-formyloxy-2-phenylacetyl, 2-acetoxy-2-phenylacetyl, 3-propionyloxy-3-phenylpropionyl, etc.), 15. phenyl and semicarbazono substituted lower alkanoyl (e.g., 2-phenyl-2-semicarbazonoacetyl, 2-semicarbazono-3-phenylpropionyl, etc.), 16. halophenylthiocarbamoyl (e.g., 2-(or 3 or 4-)chlorophenylthiocarbamoyl, 2-(or 3- or 4-)chlorophenylthiocarbamoyl, 2-(or 3- or 4-)bromophenylthiocarbamoyl, etc.), 17. phthaloyl, 18. lower alkanoylaminobenzenesulfonyl (e.g., 2-(or 3- or 4-)acetamidobenzenesulfonyl, 2-(or 3- or 4-)propionamidobenzenesulfonyl, etc.), 19. phenyl and halophenoxy substituted lower alkanoyl (e.g., 2-phenyl-2-[2-(or 3- or 4-)chlorophenoxy]acetyl, 2-phenyl-2-[2-(or 3- or 4-)bromophenoxy]acetyl, etc.), 20. halophenyl(lower)alkanoyl (e.g., 2-[2-(or 3- or 4-)chlorophenyl]acetyl, 2-[2-(or 3- or 4-)bromophenyl]acetyl, 3-[2-(or 3- or 4-)chlorophenyl]propionyl, etc.), 21. phenyl(lower)alkoxycarbonyl (e.g., benzyloxycarbonyl, phenethyloxycarbonyl, etc.), 22. hydroxyphenyl and amino substituted lower alkanoyl (e.g., 2-amino-2-[2-(or 3- or 4-)hydroxyphenyl]acetyl, 2-amino-3-[2-(or 3- or 4-)hydroxyphenyl]propionyl, etc.), 23. hydroxyphenyl and lower alkoxycarbonylamino substituted lower alkanoyl (e.g., 2-methoxycarbonylamino-2-[2-(or 3- or 4-)hydroxyphenyl]acetyl, 2-(1-cyclopropylethoxy)carbonylamino-2-[2-(or 3- or 4-)hydroxyphenyl]acetyl, 2-tertiarybutoxycarbonylamino-2-[2-(or 3- or 4-)hydroxyphenyl]acetyl, etc.), 24. phenyl and sulfo substituted lower alkanoyl (e.g., 2-phenyl-2-sulfoacetyl, 3-phenyl-3-sulfopropionyl, etc.), 25. lower alkoxyphenyl and amino substituted lower alkanoyl (e.g., 2-amino-2-[2-(or 3- or 4-)methoxyphenyl]acetyl, 2-amino-3-[2-(or 3- or 4-)methoxyphenyl]acetyl, etc.), 26. lower alkoxyphenyl and lower alkoxycarbonylamino substituted lower alkanoyl (e.g., 2-methoxycarbonylamino-2-[2-(or 3- or 4-)methoxyphenyl]acetyl, 2-(1-cyclopropylethoxy)carbonylamino-2-[2-(or 3- or 4-)methoxyphenyl]acetyl, 2-tertiarybutoxycarbonylamino-2-[2-(or 3- or 4-)methoxyphenyl]acetyl, etc.), 27. lower alkylthiophenyl and amino substituted lower alkanoyl (e.g., 2-amino-2-[2-(or 3- or 4-)methylthiophenyl]acetyl, 2-amino-3-[2-(or 3- or 4-)ethylthiophenyl]-propionyl, etc.), 28. lower alkylthiophenyl and lower alkoxycarbonylamino substituted lower alkanoyl (e.g., 2-methoxycarbonylamino-2-[2-(or 3- or 4-)methylthiophenyl]acetyl, 2-(1-cyclopropylethoxy)carbonylamino-2-[2-(or 3- or 4-)methylthiophenyl]-acetyl, 2-tertiarybutoxycarbonylamino-2-[2-(or 3- or 4-)methylthiophenyl]acetyl, 2-tertiarybutoxycarbonylamino-3-[2-(or 3- or 4-)ethylthiophenyl]propionyl, etc.), 29. lower alkylsulfinylphenyl and amino substituted lower alkanoyl (e.g., 2-amino-2-[2-(or 3- or 4-)methylsulfinylphenyl]acetyl, 2-amino-3-[2-(or 3- or 4-)ethylsulfinylphenyl]propionyl, etc.), 30. lower alkylsulfinylphenyl and lower alkoxycarbonylamino substituted lower alkanoyl (e.g., 2-methoxycarbonylamino-2-[2-(or 3- or 4-)methylsulfinylphenyl]acetyl, 2-(1-cyclopropylethoxycarbonylamino-3-[2-(or 3- or 4-)ethylsulfinylphenyl]propionyl, 2-tertiarybutoxycarbonylamino-2-[2-(or 3- or 4-)methylsulfinylphenyl]acetyl, etc.), 31. lower alkoxycarbonyl(lower)alkoxyphenyl and amino substituted lower alkanoyl (e.g., 2-amino-2-[2-(or 3- or 4-)methoxycarbonylmethoxyphenyl]acetyl, 2-amino-3-[2-(or 3- or 4-)propoxycarbonylmethoxyphenyl]propionyl, 2-amino-2-[2-(or 3- or 4-)tertiarybutoxycarbonylmethoxyphenyl]acetyl, etc.), 32. lower alkoxycarbonyl(lower)alkoxyphenyl and lower alkoxycarbonylamino substituted lower alkanoyl (e.g., 2-methoxycarbonylamino-2-[2-(or 3- or 4-)methoxycarbonylmethoxyphenyl]acetyl, 2-(1-cyclopropylethoxy)carbonyl-3-[2-(or 3- or 4-)ethoxycarbonylmethoxyphenyl]propionyl, 2-tertiarybutoxycarbonylamino-2-[2-(or 3- or 4-)tertiarybutoxycarbonylmethoxyphenyl]acetyl, etc.), 33. phenyl and thiadiazolylthio(lower)alkanoylamino substituted lower alkanoyl (e.g., N-(1,3,4-thiadiazol-2-yl)thioacetylphenylglycyl, 2-[3-(1,3,4,-thiadiazol-2-yl)thiopropionyl]amino-3-phenylpropionyl, etc.), 34. phenyl and indanyloxycarbonyl substituted lower alkanoyl (e.g., 2-phenyl-2-indanyloxycarbonylacetyl, 3-phenyl-2-indanyloxycarbonylpropionyl, etc.), 35. dihydrophenyl and amino substituted lower alkanoyl (e.g., 2-amino-2-(2,5-dihydrophenyl)acetyl, 2-amino-3-(2,5-dihydrophenyl)propionyl, etc.), 36. dihydrophenyl and lower alkoxycarbonylamino substituted lower alkanoyl (e.g., 2-methoxycarbonylamino-2-(2,5-dihydrophenyl)acetyl, 2-(1-cyclopropylethoxy)-carbonylamino-2-(2,5-dihydrophenyl)acetyl, 2-tertiarybutoxycarbonylamino-2-(2,5-dihydrophenyl)-acetyl, 2-tertiarybutoxycarbonylamino-3-(2,5-dihydrophenyl)propionyl, etc.), 37. 3-halophenyl-5-lower alkylisoxazol-4-ylcarbonyl (e.g., 3-[2-(or 3- or 4-)chlorophenyl]-5-methylisoxazol-4-ylcarbonyl, 3-[2-(or 3- or 4-)bromophenyl]-5-ethylisoxazol-4-ylcarbonyl, etc.), 38. thienyl(lower)alkanoyl (e.g., 2-(2-thienyl)acetyl, 3-(2-thienyl) propionyl, etc.), 39. thienyl and amino substituted lower alkanoyl (e.g., 2-amino-2-(2-thienyl)acetyl, 2-amino-3-(2-thienyl)-propionyl, etc.), 40. thienyl and lower alkoxycarbonylamino substituted lower alkanoyl (e.g., 2-methoxycarbonylamino-2-(2-thienyl)acetyl, 2-(1-cyclopropylethoxy)carbonylamino-2-(2-thienyl)acetyl, 2-tertiarybutoxycarbonylamino-2-(2-thienyl)acetyl, 2-tertiarybutoxycarbonylamino-3-(2-thienyl) propionyl, etc.), 41. tetrazolyl(lower)alkanoyl (e.g., 2-(1H-tetrazol-1-yl)acetyl, 3-(1H-tetrazol-1-yl)propionyl, 4-(1H-tetrazol-1-yl)butyryl, etc.), 42. thiadiazolyl(lower)alkanoyl (e.g., 2-(1,2,5-thiadiazol-3-yl)acetyl, 2-(1,3,4-thiadiazol-2-yl)acetyl, 3-(1,2,5-thiadiazol-3-yl)propionyl, etc.), 43. thiadiazolylthio(lower)alkanoyl (e.g., 2-(1,3,4-thiadiazol-2-ylthio)acetyl, 2-(1,2,5-thiadiazol -3-ylthio)acetyl, 3-(1,3,4-thiadiazol-2-ylthio)propionyl, etc.), 44. halobenzotriazolyl(lower)alkanoyl (e.g., 2-[4-(or 5- or 6- or 7-)chloro-1H-benzotriazol-1-yl]acetyl, 2-[4-(or 5- or 6- or 7-bromo-1H-benzotriazol-1-yl]acetyl, 3-[4-(or 5- or 6- or 7-)fluoro-2H-benzotriazol-2-yl]propionyl, etc.), 45. lower alkylthiadiazolyloxy(lower)alkanoyl (e.g., 2-(5-methyl-1,3,4-thiadiazol-2-yloxy)acetyl, 2-(4-methyl-1,2,5-thiadiazol-3-yloxy)acetyl, 2-(5-ethyl-1,3,4-thiadiazol-2-yloxy)propionyl, etc.), 46. dihydropropryanyl and amino substituted lower alkanoyl (e.g., 2-amino-2-(5,6-dihydro-2H-pyran-3-yl)acetyl, 2-amino-3-(5,6-dihydro-2H-pyran-3-yl)propionyl, etc.), 47. dihydropropyranyl and lower alkoxycarbonylamino substituted lower alkanoyl (e.g., 2-methoxycarbonylamino-2-(5,6-dihydro-2-H-pyran-3-yl) acetyl, 2-(1-cyclopropylethoxy)carbonylamino-2-(5,6-dihydro-2H-pyran-3-yl)acetyl, 2-tertiarybutoxycarbonylamino-2-(5,6-dihydro-2H-pyran-3-yl)acetyl, 2-tertiarybutoxycarbonylamino-3-(5,6-dihydro-2H-pyran-3-yl)propionyl, etc.), 48. sydnonyl(lower)alkanoyl (e.g., 2-(syndon-3-yl)acetyl, 3-syndon-3-yl)propionyl, etc.), and 49. phenyl(lower)alkoxycarbonyl (e.g., benzyloxycarbonyl, phenethyloxycarbonyl, etc.).

The term "a protected amino" in $R^{1a}$ and in the acylamino having a protected amino for $R^{1c}$ may include acylamino and amino group substituted by other amino protecting groups than the acyl groups as illustrated above.

The term "a protected hydroxy" in the acylamino having a protected hydroxy may include hydroxy protected by the same conventional protective groups for hydroxy as illustrated above.

The term "acylamino" in $R^{1b}$, $R^{1b'}$, the acylamino having a protected amino for $R^{1c}$, the acylamino having an amino for $R^{1d}$, the acylamino having a protected hydroxy for $R^{1e}$ and the acylamino having a hydroxy for $R^{1f}$ may include the same acylamino as illustrated above:

The term "a conventional protected carboxy group" in $R^2$ and $R^{2a}$ may include ester, acid amide, acid anhydride, salt, etc.

Suitable esters may include silyl esters, aliphatic esters and esters containing an aromatic or heterocyclic ring. The suitable silyl esters may be illustrated by examples tri(lower) alkylsilyl (e.g., trimethylsilyl, triethylsilyl, etc.) esters, etc. The suitable aliphatic esters may include saturated or unsaturated, lower or higher alkyl esters which may be branched or which may contain a cyclic ring, such as lower or higher aliphatic esters, for example, lower alkyl (e.g., methyl, ethyl, propyl, isopropyl, 1-cyclopropylethyl, butyl, tertiarybutyl, etc.) esters, higher alkyl (e.g., octykl, nonyl, undecyl, etc.) esters, lower alkenyl (e.g., vinyl, 1-propenyl, allyl, 3-butenyl, etc.) esters, lower alkynyl (e.g., 3-butynyl, 4-pentynyl, etc.) esters, lower or higher cycloalkyl (e.g., cyclopentyl, cyclohexyl, cycloheptyl, etc.) esters, etc. and lower or higher aliphatic esters containing a nitrogen, sulfur or oxygen atom, for example, lower alkoxy (lower) alkyl (e.g., methoxymethyl, ethoxyethyl, methoxyethyl, etc.) esters, lower alkylthio(lower)alkyl (e.g., methylthiomethyl, ethylthioethyl, methylthiopropyl, etc. esters, di(lower)alkylamino (e.g., dimethylamino, diethylamino, dipropylamino, etc.) esters, lower alkylideneamino (e.g., ethylideneamino, propylideneamino, isopropylideneamino, etc.) esters, lower alkylsulfenyl (lower)alkyl (e.g., methylsulfenylmethyl, ethylsulfenylmethyl, etc.) esters, etc.

The suitable esters containing an aromatic ring may include, for example, aryl (e.g., phenyl, xylyl, tolyl, naphthyl, indanyl, dihydroanthryl, etc.) esters, ar(lower)alkyl (e.g., benzyl, phenethyl, etc.) esters, aryloxy(lower)-alkyl (e.g., phenoxymethyl, phenoxyethyl, phenoxypropyl, etc.) esters, arylthio (lower)alkyl (e.g., phenylthio-methyl, phenylthioethyl, phenylthiopropyl, etc.) esters, arylsulfenyl (lower)alkyl(e.g., phenylsulfenylmethyl, phenylsulfenylethyl, etc.)aryloyl(lower)alkyl(e.g., benzoylmethyl, toluoylethyl, etc.), aryloylamino (e.g., phthalimido, etc.)esters, etc.;

The suitable esters containing an heterocyclic ring may include, for example, heterocyclic esters, heterocyclic lower alkyl esters, etc.; in which the suitable heterocyclic esters may include, for example, saturated or unsaturated, condensed or uncondensed 3 to 8-membered heterocyclic containing 1 to 4 heter-atom(s) such as an oxygen, sulfur and nitrogen atom(e.g., pyridyl, pyperidino, 2-pyridon-1-yl, tetrahydropyranyl, quinolyl, pyrazolyl, etc.) esters, etc., and the suitable heterocyclic lower alkyl esters may include, for example, saturated or unsaturated, condensed or uncondensed 3 to 8-membered heterocyclic containing 1 to 4 hetero-atom(s) such as an oxygen, sulfur and nitrogen atom(e.g., pyridyl, pyperidino, 2-pyridon-1-yl, tetrahydropyranyl, quinolyl, pyrazolyl, etc.) substituted lower alkyl (e.g., methyl, ethyl, propyl, etc.) esters, etc., The silyl esters, the aliphatic esters and the esters containing an aromatic or heterocyclic ring as mentioned above may have 1 to 10 appropriate substituent(s) such as lower alkyl (e.g., methyl, ethyl, propyl, isopropyl, butyl, tertiarybutyl, etc.), lower alkoxy(e.g., methoxy, ethoxy, propoxy, isopropoxy, butoxy, tertiarybutoxy, etc.), lower alkylthio (e.g. methylthio, ethylthio, propylthio, etc.), lower alkylsulfinyl (e.g., methylsulfinyl, ethylsulfinyl, propylsulfinyl, etc.), lower alkanesulfonyl (e.g., methanesulfonyl, ethanesulfonyl, etc.), phenylazo, halogen (e.g., chlorine, bromine, fluorine, etc.), cyano, nitro, etc., examples of which are illustrated by mono(or di or tri)halo(lower)alkyl(e.g., chloromethyl, bromoethyl, dichloromethyl, 2,2,2-trichloroethyl, 2,2,2-tribromoethyl, etc.), esters cyano(-lower) alkyl(e.g., cyanomethyl, cyanoethyl, etc.) esters, mono(or di or tri or tetra or penta)halophenyl-(e.g., 4-chlorophenyl, 3,5-dibromophenyl, 2,4,5-trichlorophenyl, 2,4,6-trichlorophenyl, pentachlorophenyl, etc.) esters. lower alkanesulfonylphenyl(e.g., 4-methanesulfonylphenyl, 2-ethanesulfonylphenyl, etc.) esters, 2-(or 3- or 4-)phenylazophenyl esters, mono(or di or tri)nitrophenyl(e.g., 4-nitrophenyl, 2,4-dinitrophenyl, 3,4,5-trinitrophenyl, etc.) esters, mono(or di or tri or tetra or penta)halophenyl(lower)alkyl(e.g., 2-chlorobenzyl, 2,4-dibromobenzyl, 3,4,5-trichlorobenzyl, pentachlorobenzyl, etc.) esters, mono(or di or tri)nitrophenyl(lower)alkyl(e.g., 2-nitrobenzyl, 2,4-dinitrobenzyl, 3,4,5-trinitrobenzyl, etc.) esters, mono-(or di or tri)(lower)alkoxyphenyl(lower)alkyl(e.g., 2-methoxybenzyl, 3,4-dimethoxybenzyl, 3,4,5-trimethoxybenzyl, etc.) esters, hydroxy and di(lower)alkylphenyl(lower)alkyl(e.g., 3,5-dimethyl-4-hydroxybenzyl, 3,5-ditertiarybutyl-4-hydroxybenzyl, etc.) esters, etc.

The suitable acid amides may include, for example, N-lower alkyl acid amide (e.g., N-methyl acid amide, N-ethyl acid amide, etc.), N,N-di(lower)alkyl acid amide(e.g., N,N-dimethyl acid amide, N,N-diethyl acid amide, N-methyl-N-ethyl acid amide, etc.), N-phenyl acid amide, or an acid amide with pyrazole, imidazole, 4-lower alkylimidazole (e.g., 4-methylimidazole, 4-ethylimidazole, etc.), etc.

The suitable acid anhydrides include, for example, an acid anhydride with a di(lower)alkyl phosphate(e.g., dimethyl phosphate, diethyl phosphate, etc.), dibenzylphosphate, phosphoric acid halide (e.g., phosphoric acid chloride, phosphoric acid bromide, etc.), di (lower)alkyl phosphite(e.g., dimethyl phosphite, diethyl phosphite, etc.), sulfurous acid, thiosulfuric acid; sulfuric acid, lower alkyl carbonate (e.g., methyl carbonate, ethyl carbonate, etc.), hydrazoic acid, hydrohalogenic acid (e.g., hydrochloric acid, hydrobromic acid, etc.), saturated or unsaturated lower aliphatic carboxylic acid (e.g., pivalic acid, pentanoic acid, isopentanoic acid, 2-ethylbutanoic acid, crotonic acid, valeric acid, propionic acid, etc.), saturated or unsaturated halo(-lower)aliphatic carboxylic acid(e.g., chloroacetic acid 3-chloro-2-pentenoic acid, 3-bromo-2-butenoic acid, etc.), substituted lower aliphatic carboxylic acid (e.g., phenylacetic acid, phenoxyacetic acid, furanacetic acid, thiopheneacetic acid, etc.), aromatic carboxylic acid (e.g., benzoic acid, etc.), or a symmetric acid anhydride, etc.

The suitable acid salts include an acid salt with a metal (e.g., sodium potassium, magnesium, etc.) or an organic amine (e.g., methylamine, diethylamine, trimethylamine, aniline, pyridine, picoline, N,N'-dibenzylethylenediamine, etc.), etc.

The term "lower alkyl" in $R^3$ means the one having straight, branched or cyclic 1 to 6 carbon chain such as methyl, ethyl, propyl, isopropyl, butyl, tert-butyl, cyclohexyl, etc.:

The term "lower alkylene" in $R^4$ means, for example, alkylene having 1 to 3 carbon atoms methylene, ethylene, propylene, etc.

The term "aryl" in $R^5$ and $R^6$ means, for example, phenyl, naphthyl, etc.

The term "a substituted aryl" in $R^5$ and $R^6$ means, for example, halophenyl such as 2(or 3 or 4)-chlorophenyl tolyl, etc.:

The term "acyl" means as illustrated above: and

The term "a residue of an acid" in Y means a group given by omitting a hydrogen atom from an acid," such as halogen(e.g., chlorine, bromine, fluorine, etc.), acyloxy(e.g., methanesulfonyloxy, benzenesulfonyloxy, toluenesulfonyloxy, etc.), and the like.

In the above and subsequent description, the term "lower" means one to six carbon chain and the term "higher" means seven to sixteen carbon chain, which may be branched or may contain a cyclic ring.

The object compound (I) in the present invention can be prepared by reacting the starting compound (II) with a base.

Suitable base used in the present reaction may include, for example, an inorganic base such as alkali metal (e.g., lithium, sodium, potassium, etc.), and alkaline earth metal (e.g., magnesium, calcium, etc.), and the corresponding hydride, lower alkoxide (e.g., methoxide, ethoxide, propoxide, butoxide, tertiary butoxide, etc.), hydroxide, carbonate, bicarbonate, amide, methyl phenyl amide, diisopropylamide, and said metal salt of butyl, phenyl or triphenylmethyl, and the like; an organic base such as primary amine (e.g., methylamine, ethylamine, propylamine, tert.-butylamine, etc.), secondary amine (e.g., dimethylamine, diethylamine, diisopropylamine, etc.) and tertiary amine (e.g., trimethylamine, triethylamine, tripropylamine, triisopropylamine, tributylamine, dimethylbenzylamine, triphenethylamine, pyrrolidine, picoline, α-picoline, N-methylpiperidine, N-methylmorpholine, N,N'-dimethylpiperazine 1,5-diazabicyclo[4,3,0]non-5-ene, 1,4-diazabicyclo[2,2,2]octane, 1,8-diazabicyclo[5,4,0]undecene-7,etc.); quarternary ammoniumhydroxide compound and the like.

The present reaction is usually carried out by using about equimolar amount of the base to the starting compound in a solvent.

When the base to be used in the present reaction is liquid, it can be also used as a solvent.

The reaction can be carried out with or without solvent, and it is preferable to conduct the reaction in a solvent.

Suitable solvent used in the present invention includes any solvent which does not give bad influence to the reaction, for example, dimethylformamide, dimethylsulfoxide, hexamethylphosphoramide, tetramethylurea, tetrahydrofuran, methylene chloride dioxane, glyme, diglyme, acetonitrile, acetone, phosphate buffer, etc.

There is no particular limitation to the present reaction temperature, and the reaction can be carried out under mild conditions such as at ambient temperature.

The present invention includes, within its scope, the case the carboxy group is changed into the protected carboxy group and the protected carboxy group is changed into the other protected carboxy group or into the free carboxy group during the reaction or post-treating in the present reaction.

When the object compound (I) is used in the next step, it can be used with or without its isolation and/or purification.

The object compound (b) can be prepared by oxidizing the compound (IA). The present oxidizing reaction is carried out under conditions so that the

group can be changed into the

group.

Oxidation in the present reaction is conducted by a conventional method such as a method of using a oxidizing agent, for example, halogen (e.g., chlorine, bromine, etc.), halogen compound (e.g., isocyanuroyl chloride, phenyliododichloride, etc.), ozone, inorganic per acid (e.g., periodic acid, persulfuric acid etc.), organic per acid (e.g., perbenzoic acid, m-chloroperbenzoic acid, performic acid, peracetic acid, chloroperacetic acid, trifluoroperacetic acid, etc.), a metal salt of the inorganic or organic peracid, hydrogen peroxide, etc.

The present reaction is preferably carried out in the presence of a compound comprising a Group Vb or VIb metal in the Periodic Table, for example, tungstic acid, molybdic acid, vanadic acid, or the like, or an alkali metal (e.g., sodium potassium, etc.), alkaline earth metal (e.g., calcium, magnesium, etc.), ammonium salt thereof, or vanadium pentoxide.

The present oxidizing reaction is usually carried out in the presence of a solvent such as chloroform, methylene chloride, lower alcohol (e.g., methanol, ethanol, etc.), pyridine, water, tetrahydrofuran, dimethylformamide, dioxane, acetic acid or any other solvent which does not give bad influence to the present reaction.

There is no particular limitation to the reaction temperature, and the present reaction is usually carried out at ambient temperature or under cooling.

The present invention includes, within its scope, the case that the carboxy group is changed into the protected carboxy group and the protected carboxy group is changed into the other protected carboxy group or into the free carboxy group during the reaction or post-treating in the present reaction.

The object compound (Ia) can be prepared by reducing the object compound (Ib).

The reducing reaction is carried out under conditions so that the

group can be changed into the -S- group.

Reduction in the present reaction is conducted by a conventional method such as a method of using stannous chloride or metal thiosulfate (e.g., sodium thiosulfate, potassium thiosulfate, etc.), or a combination of acid chloride and said stannous chloride or metal thiosulfate; or phosphorus trichloride, phosphorus pentachloride, silicon trichloride, etc. and a method described in Japanese patent official gazette No. 21111.

The present reaction is usually carried out in a solvent which does not give bad influence to the reaction, for example, dimethylformamide, acetonitrile, acetoacetic acid ester, tetrahydrofuran, chloroform, methylene chloride, dioxane, etc.

There is no limitation to the present reaction temperature, and it may be suitably selected according to the compound (Ib) and reduction method to be used in the reaction.

The present invention includes, within its scope, the case that the carboxy group is changed into the protected carboxy group and the protected carboxy group is changed into the other protected carboxy group or into the free carboxy group during the reaction or post-treating in the present reaction.

The object compound (Id) can be prepared by subjecting the compound (Ic) to elimination reaction of the protective group of the amino and the object compound (Ih) can be prepared by subjecting the compound (Ig) to elimination reaction of the protective group of the amino, respectively.

The present elimination reaction is carried out in accordance with a conventional method such as hydrolysis, using an acid, treatment with hydrazine, reduction, and the like. These methods may be selected depending on kind of the protective groups to be eliminated. When the protective group is an acyl group, it may also be eliminated by treating with an iminohalogenating agent and then with an iminoesterifying agent, if necessary, followed by hydrolysis.

The elimination reaction with the acid is one of the most commonly applied methods for eliminating the protective groups such as benzyloxycarbonyl, substituted benzyloxycarbonyl, alkoxycarbonyl, substituted alkoxycarbonyl, aralkoxycarbonyl, adamantyloxycarbonyl, trityl, substituted phenylthio, substituted aralkylidene, substituted alkylidene, substituted cycloalkylidene, etc. Suitable acid may include, for example, formic acid, trifluoroacetic acid, benzenesulfonic acid, p-toluenesulfonic acid, and the like, and the most suitable acid is an acid which can be easily distilled off under reduced pressure, for example, formic acid, trifluoroacetic acid, etc. The acid suitable for the reaction can be selected according to the protected group to be eliminated and other factors. When the elimination reaction is conducted with the acid, it is carried out in the presence of a solvent, such as a hydrophilic organic solvent, water or a mixed solvent thereof. The elimination reaction with hydrazine is commonly applied for eliminating, for example, phthaloyl. The reduction is generally applied for eliminating, for example, trichloroethoxycarbonyl, benzyloxycarbonyl, substituted benzyloxycarbonyl, 2-pyridylmethoxycarbonyl, etc. The reduction applicable for the elimination reaction of the present invention may include, for example, reduction with a metal (e.g., tin, zinc, iron, etc.) or a combination of metalic compound (e.g., chromous chloride, chromous acetate, etc.) and an organic or inorganic acid (e.g., acetic acid, propionic acid, hydrochloric acid, etc.), and reduction in the presence of a metalic catalyst for catalytic reduction. The metalic catalyst for catalytic reduction may include, for example, Raney-nickel, platinum oxide, palladium carbon and other conventional catalysts.

The protective group, trifluoroacetyl can be usually eliminated by treating with water in the presence of absence of the base, and halogen substituted-alkoxycarbonyl and 8-quinolyloxycarbonyl are usually eliminated by treating with a heavy metal such as copper, zinc, etc.

When the protective group is acyl, the acyl can be eliminated by reacting with the iminohalogenating agent and then with the imonoetherifying agent, if necessary, followed by hydrolysis. Suitable iminohalogenating agents may include, for example, phosphorus trichloride, phosphorus pentachloride, phosphorus tribromide, phosphorus pentabromide, phosphorus oxychloride, thionyl chloride, phosgene, etc. Reaction temperature in iminohalogenation is not limitative and the reaction sufficiently proceeds at ambient temperature or cooled one. Suitable iminoetherifying agents, with which the resultant in the iminohalogenating reaction is reacted, may include an alcohol such as an alkanol (e.g., methanol, ethanol, propanol, isopropanol, butanol, tertiary butanol, etc.) or the corresponding alkanol having alkoxy (e.g., methoxy, ethoxy, propoxy, isopropoxy, buthoxy, etc.) as substituents(s) at the alkyl moiety thereof, and a metal alkoxide such as alkali metal alkoxide (e.g., sodium alkoxide, potassium alkoxide, etc.) or alkaline earth metal alkoxide (e.g., calcium alkoxide, barium alkoxide, etc.) each of which is derived from the said alcohol. Reaction temperature in iminoetherification is also not limitative and the reaction sufficiently proceeds at ambient temperature or cooled one. Thus obtained reaction product is, if necessary, hydrolyzed. The hydrolysis sufficiently proceeds by pouring the reaction mixture to water or a mixture of water and a hydrophilic solvent such as methanol, ethanol, etc. In this hydrolysis, water may contain a base such as alkali metal bicarbonate, trialkylamine, etc. or an acid such as dilute hydrochloric acid, acetic acid, etc. When the protective group is acyl, the acyl can be also eliminated by hydrolysis as mentioned above or by the other conventional hydrolysis.

The reaction temperature is not limitative and may be suitably selected in accordance with the protective group for amino and the elimination method as mentioned above, and the present reaction is preferably carried out under a mild condition such as under cooling or slightly warming.

The present invention includes, within its scope, the case that the protected carboxy group is changed into the other protected carboxy group or into the free carboxy group during the reaction or post-treating in the present reaction.

The present invention also includes, within its scope, the case that when the compound (Ig) possesses furthermore one or more protected carboxy, protected hydroxy and or protected mercapto groups in the acylamino group at 6 position on penam ring, said groups are changed into corresponding free groups during the reaction.

Thus obtained compounds (Id) and (Ih) can be converted to a desirable acid addition salt thereof by a conventional method, if necessary.

The object compound (Ic) can be prepared by reacting the compound (Id) or a salt thereof with an acylating agent.

Suitable salt of the compound (Id) may include organic acid salt (e.g., acetate, maleate, tartrate, benzenesulfonate, toluenesulfonate, etc.) and inorganic acid salt (e.g., hydrochloride, sulfate, phosphate, etc.), and the like.

As acylating agents in the present reaction, there may be exemplified an aliphatic, aromatic and heterocyclic carboxylic acid, and the corresponding sulfonic acid, carbonic acid ester, carbamic acid and thio acid, and the reactive derivatives of the above acids.

As the reactive derivatives, there may be exemplified an acid anhydride, and activated amide, an activated ester, an isocyanate and an isothiocyanate, etc., example of which are illustrated by an acid azide, an mixed acid anhydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, hydrohalogenic acid (e.g., acid chloride), sulfuric acid, monoalkyl carbonate, aliphatic carboxylic acid (e.g., acetic acid, pivalic acid, pentanoic acid, isopentanoic acid, 2-ethylbutyric acid or trichloracetic acid), aromatic carboxylic acid (e.g., benzoic acid), or symmetrical acid anhydride, an acid amide with pyrazole, imidazole, 4-substituted imidazole, dimethylpyrazole, triazole or tetrazole, an ester (e.g., cyanomethyl ester, methoxymethyl ester, vinyl ester, propargyl ester, p-nitrophenyl ester, 2,4-dinitrophenyl ester, trichlorphenyl ester, pentachlorophenyl ester, methanesulfonylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or ester with N,N-dimethylhydroxylamine, 1-hydroxy-2-(1-H)-pyridone, N-hydroxysuccinimide or N-hydroxyphthalimide).

The above reactive derivatives are selected according to the kind of the acid to be used. In the acylating reaction, when free acid is used, there may be preferably added a condensing agent such as N,N'-dicyclohexylcarbodiimide, N-cyclohexyl-N'-morpholinoethylcarbodiimide, N-cyclohexy-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyldi-(2-methylimidazole), pentamethyleneketene-N-cyclohexylimide, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionylchloride, oxalyl chloride, triphenylphosphine, 2-ethyl-7-hydroxybenzisoxazolium salt, 2-ethyl-5-(m-sulfophenyl)-isoxazolium hydroxide intramolecular salt, (chloromethylene)-dimethylammonium chloride, 2,2,4,4,6,6,-hexachloro-2,2,4,4,6,6-hexahydro-1,3,5,2,4,6-triazatriphosphorine, or a mixed condensing agent such as triphenylphosphine and a carbon tetrahalide (e.g., carbon tetrachloride, carbon tetrabromide, etc.) or a halogen (e.g., chlorine, bromine, etc.), and the like.

The example of an acyl group to be introduced into the amino group in the compound (Id) by the above acylating agent may be a group dehydroxylated from each of an aliphatic, aromatic and heterocyclic carboxylic acid, and the corresponding sulfonic acid, carbonic acid ester, carbamic acid and thio acid, etc., and more particular acyl group may be the same acyl group as illustrated in the explanation of the acyl group in the acylamino group for $R^1$.

The present acylating reaction is usually carried out in a solvent which does not give bad influence to the reaction, for example, water, acetone, dioxane, acetonitrile, chloroform, methylene chloride, ethane dichloride, tetrahydrofuran, ethyl acetate, dimethylformamide, pyridine, etc., and the hydrophilic solvent mentioned above can be used. as a mixed solvent with water.

The present acylating reaction can be carried out in the presence of a base such as inorganic base (e.g., alkali metal bicarbonate, etc.) and organic base (e.g., trialkylamine, N,N-dialkylamine, N,N-dialkylbenzylamine, pyridine, 1,5-diazabicyclo[4,3,0]non-5-ene, 1,4-diazabicyclo[2,2,2]octane, 1,8-diazabicyclo[5,4,0]undecene-7, etc.).

In the present reaction, a liquid base or liquid condensing agent can be also used as a solvent.

There is no limitation to the present reaction temperature, and the present reaction can be carried out at cooled or at ambient temperature.

The present invention may include the case that the protected carboxy is changed into the other protected carboxy group or into the free carboxy group in the present reaction or post-treating in the present reaction.

The object compound (If) can be prepared by reacting the compound (Ie) with an iminohalogenating agent, an iminoetherifying agent and then an acylating agent, if necessary, followed by hydrolysis.

Suitable iminohalogenating agents may include, for example, phosphorus trichloride, phosphorus pentachloride, phosphorus tribromide, phosphorus pentabromide, phosphorus oxychloride, thionyl chloride, phosgene, etc. Reaction temperature for iminohalogenation is not limitative and the reaction sufficiently proceeds at ambient temperature or cooled one.

Suitable iminoetherifying agents, with which the resultant in the iminohalogenating reaction is reacted, may include an alcohol such as an alkanol (e.g., methanol, ethanol, propanol, isopropanol, butanol, tertiary butanol, etc.) or the corresponding alkanol having alkoxy (e.g., methoxy, ethoxy, propoxy, isopropoxy, buthoxy, etc.) as substituent(s) at the alkyl moiety thereof and a metal alkoxide such as alkali metal alkoxide (e.g., sodium alkoxide, potassium alkoxide, etc.) or alkaline earth metal alkoxide (e.g., calcium alkoxide, barium alkoxide, etc.) derived from the said alcohol. The reaction temperature for iminoetherification is also not limitative and the reaction sufficiently proceeds at ambient temperature or cooled one.

The present acylating reaction can be carried out under the similar conditions as described in the acylating reaction of the compound (Id).

Thus obtained reaction product is, if necessary, hydrolyzed. The hydrolysis sufficiently proceeds by pouring the reaction mixture to water or a mixture of water and a hydrophilic solvent such as methanol, ethanol, etc. In this hydrolysis, water may contain a base such as alkali metal bicarbonate, trialkylamine, etc. or an acid such as dilute hydrochloric acid, acetic acid, etc.

In the present reaction, the acylamino group $R^{1b}$ in the compound (Ie) is changed to the other acylamino group for $R^{1b\,\prime}$ in the compound (If).

The object compound (Ij) can be prepared by subjecting the compound (Ii) to elimination reaction of the protective group of hydroxy.

The present elimination reaction is carried out in accordance with a conventional method such as a method of using an acid or a base, reduction, and the like. These methods may be selected depending on kind of the protective groups to be eliminated. The elimination reaction with the acid is one of the most commonly applied methods for eliminating the protective groups such as benzyloxycarbonyl, substituted benzyloxycarbonyl, alkoxycarbonyl, substituted alkoxycarbonyl, aralkoxycarbonyl, adamantyloxycarbonyl, trityl, substituted phenylthio, substituted aralkylidene, substituted alkylidene, substituted cycloalkylidene, etc. Suitable acid may include, for example, formic acid, trifluoroacetic acid, benzenesulfonic acid, p-toluenesulfonic acid, and the like, and the most suitable acid is an acid which can be easily distilled off under reduced pressure, for example, formic acid, trifluoroacetic acid, etc. The acid suitable for the reaction can be selected according to the protected group to be eliminated and other factors. When the elimination reaction with the acid may be carried out in the presence of a solvent, such as a hydrophilic organic solvent, water or a mixed solvent thereof. The elimination reaction with the base is applied for eliminating acyl group.

Suitable base may include, for example, an inorganic base such as alkali metal (e.g., sodium, potassium, etc.), alkaline earth metal (e.g., magnesium, calcium, etc.), the hydroxide or carbonate or bicarbonate thereof, and the like, or an organic base such as trialkylamine (e.g., trimethylamine, triethylamine, etc.), picoline, N-methylpyrrolidine, N-methyl morpholine, 1,5-diazabicyclo[4,3,0]non-5-ene, 1,4-diazabicyclo[2,2,2]octane, 1,8-diazabicyclo[5,4,0]undecene-7, and the like. The elimination reaction with the base is often carried out in water or a hydrophilic organic solvent or a mixed solvent thereof.

The reduction is generally applied for eliminating, for example, trichloroethoxycarbonyl, benzyloxycarbonyl, substituted benzyloxycarbonyl, 2-pyridylmethoxycarbonyl, etc.

The reduction applicable for the elimination reaction of the present invention may include, for example, reduction using a metal (e.g., tin, zinc, iron, etc.) or a combination of metalic compound (e.g., chromous chloride, chromous acetate, etc.) and an organic or inorganic acid (e.g., acetic acid, propionic acid, hydrochloric acid, etc.), and reduction in the presence of a metalic catalyst for catalytic reduction. The metalic catalysts for catalytic reduction may include, for example, Raney-nickel, platinum oxide, palladium carbon and other conventional catalysts. The protective group, trifluoroacetyl can be usually eliminated by treating with water in the presence or absence of the base, and halogen substituted-alkoxycarbonyl and 8-quinolyloxycarbonyl are usually eliminated by treating with a heavy metal such as copper, zinc, etc.

When the protective group is trifluoroacetyl, it can be eliminated by treating with water or water in the presence of a base, and when the protective group is halogen substituted alkoxycarbonyl or 8-quinolyloxycarbonyl, those can be eliminated by treating with a heavy metal such as copper, lead, and the like.

When the protective group is acyl, the acyl can be eliminated by hydrolysis as mentioned above or by other conventional hydrolysis.

The reaction temperature is not limitative and may suitably selected in accordance with the protective group for hydroxy and the elimination method, and the present reaction is preferably carried out under a mild condition such as under cooling or slightly warming.

The present invention include, within its scope, the case that the protected carboxy group is changed into the other protected carboxy group or into the free carboxy group during the reaction or post-treating in the present reaction.

The present invention also include, within its scope, the case that when the compound (Ii) possesses furthermore one or more protected amino, protected carboxy and/or, protected mercapto groups in the acylamino group at 6 position on penam ring, said groups are changed into corresponding free groups during the reaction.

The object compound (Il) can be prepared by subjecting the compound (Ik) to elimination reaction of the protective group of the carboxy.

In the present elimination reaction, all conventional methods used in the elimination reaction, all conventional methods used in the elimination reaction of the protected carboxy, for example, reduction, hydrolysis, etc. can be applicable. When the protected group is an active ester, active amide or acid anhydride, those can be eliminated by hydrolysis, usually eliminated under mild hydrolysis conditions such as by contacting with water. The reduction can be applicable for eliminating, for example, 2-iodoethyl ester, 2,2,2-trichloroethyl ester, benzyl ester, etc. The elimination reaction with an acid can be applicable for eliminating the protected groups such as p-methoxybenzyl ester, tert-butyl ester, tert-pentyl ester, trityl ester, diphenylmethyl ester, bis(-methoxyphenyl)methyl ester, 3,4-dimethoxybenzyl ester, 1-cyclopropylethyl ester, and the like. The elimination reaction with an anhydrous basic catalyst can be applicable for eliminating the protective groups such as ethynyl ester, 4-hydroxy-3,5-di(tert-butyl)benzyl ester, and the like. The reduction applicable for the elimination reaction of the present invention may include, for example, reduction using a combination of a metal (e.g., zinc, zinc amalgam, etc.) or a chrome salt compound (e.g., chromous chloride, chromous acetate, etc.) and an organic or inorganic acid (e.g., acetic acid, propionic acid, hydrochloric acid, etc.), and reduction in the presence of a metalic catalytic reduction. The metalic catalysts for catalytic reduction include, for example, platinum catalyst (e.g., platinum wire, spongy platinum, platinum black, platinum colloid, etc.), palladium catalyst (e.g., palladium spongy, palladium black, palladium oxide, palladium on barium sulfate, palladium on barium carbonate, palladium on charcoal, palladium on silica gel, palladium colloid, etc.), nickel catalyst (e.g., reduced nickel, nickel oxide, Raney nickel, Urushibara nickel, etc.), etc. Suitable acid used for the elimination reaction may include, for example, formic acid, trihaloacetic acid (e.g., trichloroacetic acid, trifluoroacetic acid, etc.), hydrochloric acid, hydrofluoric acid, p-toluenesulfonic acid, trifluoromethanesulfonic acid, mixed acid of hydrochloric acid and acetic acid, etc.), etc. Suitable anhydrous basic catalyst for the elimination reaction may include, for example, sodium thiophenolate, $(CH_3)_2LiCu$, etc. When the protective group is eliminated by treating with water or a liquid acid in the reaction, the present reaction can be carried out without solvent. In the present reaction, can be used any solvent which does not give bad influence to the present reaction, for example, dimethylformamide, methylene chloride, chloroform, tetrahydrofuran, acetone, and the like. There is no particular limitation to the reaction temperature, and it may suitably selected according to the starting compound and an elimination method to be practically applied. The present invention includes the case that a protected carboxy, hydroxy, mercapto or amino group contained in the starting compound is changed into each free carboxy, hydroxy, mercapto or amino group, respectively, in the course of or post-treating in the present reaction. Thus obtained compound (II) can be converted to a desirable metal (e.g., sodium, potassium, etc.) salt or organic base salt thereof, if necessary.

The object compound (In) can be prepared by reacting the compound (Im) with semicarbazide or a salt thereof.

Suitable salt of semicarbazide may include an inorganic acid salt (e.g., hydrochloride, sulfate, etc.) and an organic acid salt (e.g., acetate, maleate, tartrate, etc.), and the like.

The present reaction is usually carried out in a solvent which does not give bad influence to the reaction, for example, methanol, ethanol, water, acetonitrile, chloroform, ether, formamide, benzene, etc.

The present reaction is preferably carried out in the presence of a base.

Suitable base may include, for example, an inorganic base such as alkali metal (e.g., lithium, sodium, potassium, etc.) and alkaline earth metal (e.g., magnesium, calcium, etc.), and the corresponding hydride or amide or alkoxide (e.g., methoxide, ethoxide, propoxide, butoxide, tert.-butoxide, etc.) or hydroxide or carbonate or bicarbonate or acetate and the like, and an organic base such as tert.-amine (e.g., trimethylamine, triethylamine, tripropylamine, triisopropylamine, tributylamine, dimethylbenzylamine, triphenethylamine, pyrrolidine, pyridine, α-picoline, N-methylpiperidine, N-methylmorpholine, N,N′-dimethylpiperazine, 1,5-diazabicyclo[4,3,0]non-5-ene, 1,4-diazabicyclo[2,2,-2]octane, 1,8-diazabicyclo[5,4,0]undecene-7, etc.), quarternary ammoniumhydroxide compound, and the like.

There is no particular limitation to the reaction temperature, and the present reaction is usually carried out under warming to heating about at boiling point of a solvent used in the present reaction.

The present invention includes, within its scope, the case that the protected carboxy group is changed into the other protected carboxy group or into the free carboxy group during the reaction or post-treating in the present reaction.

The object compound (Ip) can be prepared by reacting the compound (Io) with an acylating agent under reduction conditions.

The present acylating reaction is carried out under conditions that the

group can be changed into the -S- group that is, the same conditions as those under which the compound (Ia) is prepared by reducing the compound (Ib).

Suitable acylating agent is the same as that used in the acylating reaction of the compound (Ie).

The present reaction is preferably carried out by using an acid halide as an acylating agent. The present invention is usually carried out in a solvent which does not give bad influence to the reaction, for example, dimethylformamide, acetonitrile, acetoacetic acid ester, tetrahydrofuran, chloroform, methylene chloride, dioxane, etc. There is no particular limitation to the reaction temperature, and the reaction temperature can be selected according to the compound (Io), acylating agent and reduction method to be used.

The present invention includes, within its scope, the case that the carboxy group is changed into the protected carboxy and the protected carboxy is changed into the other protected carboxy or into free carboxy group during the present reaction or post-treating in the present reaction.

The object compounds (I) of this invention have antimicrobial activities against various pathogenic microorganisms and may be useful for treatment of diseases infected by such microorganisms in human and animals.

With regard to representative object compounds of this invention, antimicrobial activities are illustrated for reference in the following. The MIC values (mcg/ml) against *Staphylococcus aureus* 209-P JC-1 and *Bacillus subtilis* ATCC6633 of the object compounds (I) are shown below.

Method for estimation of antimicrobial activity in vitro:

In vitro antimicrobial activity was determined by the two-fold agar-plate dilution method as described below. One loopful of an overnight culture of each test strain in Trypticasesoy broth ($10^6$ viable cells per ml) was streaked on heart infusion agar (HI-agar) containing graded concentrations of antibiotics, and the minimal inhibitory concentration (MIC) was expressed in terms of mcg/ml after incubation at 37°C for 20 hours.

1. 2-Methyl-2,3-methylene-6-phenylglycylaminopenam-3-carboxylic acid
   S. aur.:25; B. sub.:1.56
2. N,N′-dibenzylethylenediamine salt of 2-methyl-2,3-methylene-6-[3-(2-chlorophenyl)-5-methylisoxazol-4-carboxamido]penam-3-carboxylic acid
   S. aur.:50; B. sub.:12.5

3. 2-Methyl-2,3-methylene-6-[2-(2-thienyl)acetamido]penam-3-carboxylic acid
S. aur.:12.5; B. sub.:1.56

4. N,N'-dibenzylethylenediamine salt of 2-methyl-2,3-methylene-6-[2-(2-chlorophenoxy)-2-phenylacetamido]penam-3-carboxylic acid
S. aur.:1.56; B. sub.:1.56

5. Sodium 2-methyl-2,3-methylene-6-[2-(1,3,4-thiadiazol-2-ylthio)acetamido]penam-3-carboxylate
S. aur.:12.5; B. sub.:3.13

6. Sodium 2-methyl-2,3-methylene-6-(2-methylthioacetamido)penam-3-carboxylate
S. aur.:12.5; B. sub.:3.13

7. Sodium 2-methyl-2,3-methylene-6-(2-formyloxy-2-phenylacetamido)penam-3-carboxylate
S. aur.:12.5; B. sub.:1.56

8. Sodium 2-methyl-2,3-methylene-6-(2-hydroxy-2-phenylacetamido)penam-3-carboxylate
S. aur.:12.5; B. sub.:313

9. N,N'-dibenzylethylenediamine salt of 2-methyl-2,3-methylene-6-phthalimidopenam-3-carboxylic acid
S. aur.:200, B. sub.:50

10. 2-Methyl-2,3-methylene-6-(2-phenyl-2-semicarbazono)acetamidopenam-3-carboxylic acid
S.aur.:50; B. sub.:3.13

11. N,N'-Dibenzylethylenediamine salt of 2-methyl-2,3-methylene-6-(1-cyclopropylethoxy)carbonylaminopenam-3-carboxylic acid
S.aur.:6.25; B. sub.:6.26

12. 2-Methyl-2,3-methylene-6-(2-phenylacetamido)penam-3-carboxylic acid
S.aur.:25; B. sub.:3.13

13. 2-Methyl-2,3-methylene-6-[2-(1H-tetrazol-1-yl)acetamido]-penam-3-carboxylic acid
S.aur.:50; B. sub.:12.5

The object compounds(I) of this invention are also useful as a key intermediate for preparing and antimicrobial compound, for example, 2-loweralkyl-7-acylamino-3-cephem-4-carboxylic derivatives.

The compound (I) of the present invention may be formulated for administration in any convenient way by analogy with other antibiotics substances.

Thus, the composition comprising the compounds (I) can be used in the form of pharmaceutical preparations, for example, in solid, semisolid or liquid form, which contain the active object compound (I) in admixture with a pharmaceutical or inorganic carrier or excipient suitable for external or parenteral applications. The active ingredient may be compounded, for example, with the usual carriers for tablets, pellets, capsules, suppositories, solutions, emulsions, aqueous suspensions and other form suitable for use. The carriers which can be used are glucose, lactose, gum acacia, gelatin, mannitol, starch paste, magnesium trisilicate, talc, corn starch, keratin, colloidial silica, potato starch, urea and other carriers suitable for use in manufacturing preparations, in solid, semisolid or liquid form, and in addition auxiliary, stabilizing, thickening and coloring agents can be contained in the compositions of this invention. The compositions of this invention can also contain preservative or bacteriostatic agents thereby keeping the active ingredient in the desired preparations stable in activity. The active object compound (I) is included in the compositions of this invention in an amount sufficient to produce the desired therapeutic effect upon the bacterially infected process or condition. While the dosage or therapeutically effective quantity of the compound varies from and also depends upon the age and condition of each individual patient being treated, a daily dose of about 0.5 – 5 g., preferably 1 – 2 g/day of the active ingredient is generally given for treating diseases against which the object compound (I) is useful.

Having now generally described the invention, a further understanding can be attained by reference to certain specific examples which are provided herein for purposes of illustration only and are not intended to be construed as limiting unless otherwise so indicated.

Reaction of:

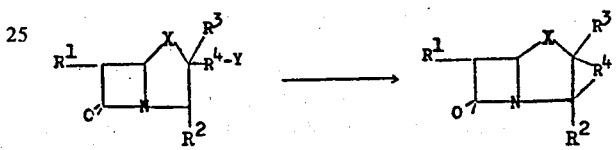

EXAMPLE 1

To a solution of 2,2,2-trichloroethyl 2-bromomethyl-2-methyl-6-(2-phenylacetamido)penam-3-carboxylate-1-β-oxide(5.61 g.) in dimethylformamide(50 ml.) was added a solution of 1,8-diazabicyclo [5,4,0] undecene-7(1.67 g.) in dimethylformamide(5ml.) at −45° to −50°C. After stirring the mixture at −50°C for 3 hours, the cooling bath was removed and the mixture was stirred till the inner temperature rises 0° to −10°C. The resultant mixture was poured into an ice-cooled solution of ethyl acetate and diluted hydrochloric acid, and the ethyl acetate layer was separated and the aqueous solution extracted with ethyl acetate. The ethyl acetate layers were combined together, washed with water and then dried over magnesium sulfate. After treatment with activated charcoal, the solvent was removed and then the residue was washed with ether to give colorless crystals of 2,2,2-trichloroethyl 2-methyl-2,3-methylene-6-(2-phenylacetamido)penam-3-carboxylate-1-β-oxide(3.64 g.)., mp. 148° to 148.5°C.

Analysis: $C_{18}H_{17}N_2O_5SCl_3$: Calcd.: C45.06, H3.57, N5.84, C122.17, S6.68; Found: C44.82, H3.50, N5.72, C122.11, S7.04

Results obtained by carrying out the Example 1 under various conditions are shown in the following Table 1.

(Table 1)

| No. | Base | Solvent | Reaction temperature | Reaction time | | Yield (%) |
|---|---|---|---|---|---|---|
| 1 | $K_2CO_3$ | dimethylformamide | room temperature | 14 | hours | 38 |
| 2 | " | hexamethylphosphoramide | " | 48 | " | 28 |
| 3 | " | acetone | " | 40 | " | 30 |
| 4 | triethylamine | " | " | 72 | " | 26 |
| 5 | " | dimethylsulfoxide | " | 19 | " | 37 |
| 6 | triethylamine-$Li_2CO_3$ tert- | dimethylformamide | " | 20 | " | 42 |

(Table 1)-continued

| No. | Base | Solvent | Reaction temperature | Reaction time | Yield (%) |
|---|---|---|---|---|---|
| 7 | butylamine | dimethylsulfoxide | " | 2 " | 31 |
| 8 | N-ethylpiperidine | dimethylformamide | " | 40 " | 43 |
| 9 | " | dimethylsulfoxide | 50 to 55°C | 3 " | 47 |
| 10 | Potassium tert-butoxide | " | room temperature | 2 " | 33 |
| 11 | 1,8-diazabi-cyclo[5,4,0]undecene-7 | dimethylformamide | −10°C | 1 " | 58 |

EXAMPLE 2

Potassium carbonate (0.08 g.) was added to a solution of 2,2,2-trichloroethyl 2-bromomethyl-2-methyl-6-(2-phenylacetamido)penam-3-carboxylate-1-β-oxide(0.56 g.) in dried dimethylformamide(5 ml.) and stirred at room temperature for 5 hours. The mixed solution was poured into ice-water, acidified with phosphoric acid and then extracted with ethyl acetate. The ethyl acetate extract was washed with water, a saturated aqueous solution of sodium bicarbonate, and water in turn, and then dried over magnesium sulfate. The solvent was removed under reduced pressure, and the residue was purieied by column chromatography on silica gel using chloroform as developing solvent. The purified product was crystallized with ether to give colorless needles of 2,2,2-trichloroethyl 2-methyl-2,3-methylene-6-(2-phenylacetamido)penam-3-carboxylate-1-β-oxide(130 mg.), mp. 142° to 143°C.

Analysis: $C_{18}H_{17}N_2O_5SCl_3$: Calcd.: C45.06, H3.57, N5.83, S6.68, C122.17; Found: C44.92, H3.42, N5.81, S6.35, C122.03

EXAMPLE 3

To a suspension of 2,2,2-trichloroethyl 2-bromomethyl-2-methyl-6-aminopenam-3-carboxylate-1-β-oxide hydrochloride(14.4 g.) in dimethylformamide(100 ml.) was dropwise added a solution of 1,8-diazabicyclo[5,4,0]undecene-7(9.13 g.) in dimethylformamide(5 ml.) under cooling at −50° to −55°C over 20 minutes and then stirred for 3 hours. After the reaction the resultant mixture was poured into a solution of ethyl acetate (500 ml.) and ice-water (300 ml.), and the ethyl acetate layer was separated and washed twice with water and a saturated aqueous solution of sodium chloride in turn. The extract was dried over magnesium sulfate, treated with activated charcoal and concentrated under reduced pressure. The residue was dissolved in ethyl acetate (70 ml.). A solution of p-toluenesulfonic acid-monohydrate(5.7 g.) in ethyl acetate(50 ml.) was added to the solution and crystals precipitated were collected by filtration. The crystals were recrystallized from methanol to give 2,2,2-trichlolo-ethyl 2-methyl-2,3-methylene-6-aminopenam-3-carboxylate-1-β-oxide toluenesulfonate (13.0 g.), mp. 176° to 179°C.

Analysis: $C_{17}H_{19}N_2O_7SCl_3$: Calcd.: C38.24, H3.59, N5.25, S12.01; Found: C38.11, H3.51, N5.25, S11.80

EXAMPLE 4

To a solution of 2,2,2-trichloroethyl 2-methyl-2-bromomethyl-6-(2-phenylacetamido)penam-3-carboxylate(1.08 g.) in dimethylformamide (10 ml.) was added 1,8-diazabicyclo[5,4,0]undecene-7(360 mg.) under cooling at −50° to −60°C and stirred at the same temperature for an hour The inner temperature of the reaction mixture was raised to −10°C. The mixture was poured into a solution of ethyl acetate and dilute phosphoric acid and then extracted. The extract was washed with dilute phosphoric acid, water, a saturated aqueous solution of sodium bicarbonate and water in turn, treated with activated charcoal and dried over magnesium sulfate. After removing the solvent, the residue was purified by column chromatography on silica gel using chloroform as developing solvent to give 2,2,2-trichloroethyl 2-methyl-2,3-methylene-6-(2-phenylacetamido)penam-3-carboxylate(360 mg.), mp. 140° to 143°C.

EXAMPLE 5

To a solution of 2,2,2-trichloroethyl 2-bromomethyl-2-methyl-6-[2-(1,2,5-thiadiazol-3-yl)acetamido]-penam-3-carboxylate-1-β-oxide (0.57 g.) in dimethylformamido (6 ml.) was dropwise added over 15 minutes a solution of 1,8-diazabicyclo[5,4,0]undecene-7(0.167 g.) in dimethylformamide (2 ml.) under stirring and cooling at −45° to −50°C, and the reaction temperature was gradually elevated to −15°C over 1.5 hours. After the reaction, the reaction mixture was poured into a mixture of ethyl acetate (15 ml.), cooled water (15 ml.) and 10% hydrochloric acid (1 ml.) and extracted with ethyl acetate. The extract was washed twice with 3% hydrochloric acid (10 ml.) and twice a saturated sodium chloride aqueous solution (10 ml.) and then dried over magnesium sulfate. After drying, the solution was treated with activated charcoal and the gummy material obtained by distilling off the solvent was pulverized from a mixture of ether and n-hexane to give 2,2,2-trichloroethyl 2-methyl-2,3-methylene-6-[2-(1,2,5-thiadiazol-3-yl)-acetamido]penam-3-carboxylate-1-β-oxide (0.31 g.).

Infrared Absorption Spectrum (Nujol): 3350, 1790, 1747, 1680 cm$^{-1}$

EXAMPLE 6

To a solution of 2,2,2-trichloroethyl 2-bromomethyl-2-methyl-6-(2-methylthioacetamido)penam-3-carboxylate-1-β-oxide(0.53 g.) in dimethylformamide (5 ml.) was dropwise added over 3 minutes a solution of 1,8-diazabicyclo[5,4,0]undecene-7(0.17 g.) in dimethylformamide (2 ml.) under stirring and cooling at −50°C, and the reaction temperature was gradually elevated to −10°C over 2 hours. A mixture of ethyl acetate(30 ml.), cooled water (30 ml.) and 10% hydrochloric acid (1 ml.) was added all at once to the reaction mixture and the solution was stirred enough, treated with activated charcoal and then the ethyl acetate layer was separated. The ethyl acetate layer was washed twice with 3% hydrochloric acid (20 ml.) and twice a saturated sodium chloride aqueous solution (20 ml.) in turn, dried over magnesium sulfate, treated with activated charcoal, after which the solvent was distilled off. The obtained residue was washed with a mixture of ether and n-hexane to give 2,2,2-trichloroethyl 2-methyl-2,3-methylene-6-(2-methylthioacetamido)penam-3-carboxylate-1-$\beta$-oxide (0.33 g.), mp. 169° to 170°C.

EXAMPLE 7

To a solution of 2,2,2-trichloroethyl 2-bromomethyl-2-methyl-6-(2-phenoxyacetamido)penam-3-carboxylate-1-$\beta$-oxide(5.58 g.) in anhydrous dimethylformamide (60 ml.) was dropwise added over 5 minutes 1,8-diazabicyclo[5,4,0]undecene-7(1.78 g.) under stirring and cooling at −45° to −50°C, and the mixture was stirred for 3.7 hours. After the reaction, the reaction mixture was poured into a mixture of ethyl acetate (100 ml.) and ice-water (100 ml.) and the ethyl acetate layer was separated, after which the aqueous layer was further extracted twice with ethyl acetate. The combined extract was washed with dilute hydrochloric acid, a saturated sodium bicarbonate aqueous solution and a saturated sodium chloride aqueous solution in turn and then dried over magnesium sulfate. After drying, the solution was treated with activated charcoal and the solvent was removed. The obtained oily material was purified by column chromatography on silica gel using chloroform as developing solvent to give oily 2,2,2-trichloroethyl 2-methyl-2,3-methylene-6(2-phenoxyacetamido)penam-3-carboxylate-1-$\beta$-oxide(3.0 g.).
Infrared Absorption Spectrum (Chloroform);: 3350, 1800, 1750, 1687 cm$^{-1}$ The following compounds were obtained by using the similar manner as described in Examples 1 to 7.

1. 2,2,2-Trichloroethyl 2-methyl-2,3-methylene-6-[2-(1H-tetrazol1-yl)acetamido]penam-3-carboxylate(mp. 133° to 137°C.).
2. 2,2,2-Trichloroethyl 2-methyl-2,3-methylene-6-(2-thienyl)acetamidopenam-3-carboxylate (mp. 144° to 145°C)
3. 2,2,2-Trichloroethyl 2-methyl-2,3-methylene-6-(3-phenylureido)penam-3-carboxylate (mp. 153.5° to 155°C)
4. 2,2,2-Trichloroethyl 2-methyl-2,3-methylene-6-[2-phenyl-2(2-chlorophenoxy)acetamido]penam-3-carboxylate, oil.
5. 2,2,2-Trichloroethyl 2-methyl-2,3-methylene-6-(2-phenyl-2-formyloxyacetamido)penam-3-carboxylate, oil.
6. 2,2,2-Trichloroethyl 2-methyl-2,3-methylene-6-[2-(1,3,4-thiadiazol-2-ylthio)acetamido]penam-3-carboxylate, oil.
7. 2,2,2-Trichloroethyl 2-methyl-2,3-methylene-6-[2-(5-chloro-1H-benzotriazol-1-yl)acetamido]penam-3-carboxylate (mp. 164° to 166°C)
8. 2,2,2-Trichloroethyl 2-methyl-2,3-methylene-6-(2-methylthioacetamido)penam-3-carboxylate, oil.
9. 2,2,2-Trichloroethyl 2-methyl-2,3-methylene-6-(1-cyclopropylethoxy) carbonylaminopenam-3-carboxylate, oil.
10. 2,2,2-Trichloroethyl 2-methyl-2,3-methylene-6-[N-(1-cyclopropylethoxy)carbonylphenylglycyl-]aminopenam-3-carboxylate, amorphous.
11. 2,2,2-Trichloroethyl 2-methyl-2,3-methylene-6-[3-(2-Chlorophenyl)-5-methylisoxazol-4-carbonamido]penam-3-carboxylate, foam.
12. 2,2,2-Trichloroethyl 2-methyl-2,3-methylene-6-phenylglyoxylamidopenam-3-carboxylate(mp. 132° to 133°C).
13. 2,2,2-Trichloroethyl 2-methyl-2,3-methylene-6-(phenylthio)carbonylaminopenam-3-carboxylate, mp. 121°C.
14. 2,2,2-Trichloroethyl 2-methyl-2,3-methylene-6-(4-acetamidobenzenesulfonamido)penam-3-carboxylate (mp. 193° to 198°C)
15. 2-Methyl-2,3-methylene-6-(2-phenylacetamido)penam-3-carboxylic acid[mp. 112° to 118°C (dec.)]
16. 2-Methyl-2,3-methylene-6-[2-(1H-tetrazol-1-yl)-acetamido]penam-3-carboxylic acid [mp. 167° to 170°C (dec.)]
17. 2-Methyl-2,3-methylene-6-[2-(2-thienyl)acetamido] penam-3-carboxylic acid [mp. 106° to 108°C (dec.)]
18. 2-Methyl-2,3-methylene-6-(3-phenylureido)penam-3-carboxylic acid [mp. 108° to 110°C (dec.)].
19. N,N'-Dibenzylethylenediamine salt of 2-methyl-2,3-methylene-6-[2-phenyl-2-(2-chlorophenoxy) acetamido] penam-3-carboxylic acid [mp. 107° to 110°C (dec.)]
20. 2-Methyl-2,3-methylene-6-(2-phenyl-2-formyloxyactamido)penam-3-carboxylic acid, oil.
21. Sodium salt of 2-methyl-2,3-methylene-6-[2-(1,3,4-thiadiazol-2-ylthio) acetamido] penam-3-carboxylic acid, (mp. 171 to 177°C)
22. Sodium salt of 2-methyl-2,3-methylene-6-(2-methylthioacetamido) penam-3-carboxylic acid [mp. 178° to 181°C (dec.)]
23. N.N'-Dibenzylethylenediamine salt of 2-methyl-2,2-methylene-6-(1-cyclopropylethoxy) carbonylaminopenam-3-carboxylic acid [mp. 148° to 149.5°C (dec.)]
24. 2-Methyl-2,3-methylene-6-[N-(1-cyclopropylethoxy)carbonylphenylglycylamino]penam-3-carboxylic acid, amorphous.
25. N, N'-Dibenzylethylenediamine salt of 2-methyl-2,3-methylene-6-[3-(2-chlorophenyl)-5-methylisoxazol-4-carbonamido]penam-3-carboxylic acid [mp. 97° to 100°C (dec.)]
26. Sodium salt of 2-methyl-2,3-methylene-6-(2-hydroxy-2-phenylacetamido)penam-3-carboxylic acid [mp. 180° to 190°C (dec.)]
27. 2-Methyl-2,3-methylene-6-(2-phenyl-2-carbamoylhydrazonoacetamido) penam-3-carboxylic acid [mp. 198° to 199°C (dec.)]
28. 2-Methyl-2,3-methylene-6-[1-(4-chlorophenyl)imino-1-acetylthiomethyl]aminopenam-3-carboxylic acid [mp. 147° to 150°C (dec.)]
29. 2-Methyl-2,3-methylene-6-(phenylthio)carbonylaminopenam-3-carboxylic acid [mp. 116° to 119°C (dec.)]
30. 2-Methyl-2,3-methylene-6-(4-acetamidobenzenesulfonamido)penam-3-carboxylic acid [mp. 230°C (dec.)]
31. 2,2,2-Trichloroethyl 2-methyl-2,3-methylene-6-[2-(1H-tetrazol-1-yl)acetamido]penam-3-carboxylate-1-$\beta$-oxide [mp. 189° to 192°C. (dec.)]
32. 2,2,2-Trichloroethyl 2-methyl-2,3-methylene-6-[2-(2-thienyl) acetamido]penam-3-carboxylate-1-$\beta$-oxide [mp. 118.5° to 122°C (dec.)]
33. 2,2,2-Trichloroethyl 2-methyl-2,3-methylene-(3-phenylureido)penam-3-carboxylate-1-$\beta$-oxide (mp.d 167.5° to 169.5°C)
34. 2,2,2-Trichloroethyl 2-methyl-2,3-methylene-6-[2-phenyl-(2-chlorophenoxy)acetamido]penam-3-carboxylate-1-$\beta$-oxide, oil.

35. 2,2,2-Trichloroethyl 2-methyl-2,3-methylene-6-(2-phenyl-2-formyloxyacetamido)penam-3-carboxylate-1-β-oxide (mp. 151.5° to 153.5°C)
36. 2,2,2-Trichloroethyl 2-methyl-2,3-methylene-6-[2-(1,3,4-thiadiazol-2-ylthio)acetamido]penam-3-carboxylate-1-β-oxide, oil.
37. 2,2,2-Trichloroethyl 2-methyl-2,3-methylene-6-[2-(5-chloro-1H-benzotriazol-1-yl)acetamido]penam-3-carboxylate-1-β-oxide ]mp. 145° to 149°C (dec.)]
38. 2,2,2-Trichloroethyl 2-methyl-2,3-methylene-6-(2-methylthioacetamido)penam-3-carboxylate-1-β-oxide (mp. 177°C)
39. 2,2,2-Trichloroethyl 2-methyl-2,3-methylene-6-[3-(4-chlorophenyl)thioureido]penam-3-carboxylate-1-β-oxide [mp. 180° to 190°C (dec.)]
40. 2,2,2-Trichloroethyl 2-methyl-2,3-methylene-6-(1-cyclopropylethoxy)carbonylaminopenam-3-carboxylate-1-β-oxide, oil.
41. 2,2,2-Trichloroethyl 2-methyl-2,3-methylene-6-[N-(1-cyclopropylethoxycarbonylphenylglycyl-]aminopenam-3-carboxylate-1-β-oxide, foam.
42. 2,2,2-Trichloroethyl 2-methyl-2,3-methylene-6-[3-(2-chlorophenyl)-5-methylisoxazol-4-carbonamido]penam-3-carboxylate-1-β-oxide, amorphous.
43. 2,2,2-Trichloroethyl 2-methyl-2,3-methylene-6-phenylglyoxylamidopenam-3-carboxylate-1-β-oxide [mp. 175° to 176°C (dec.)]
44. N,N dibenzylethylenediamine salt of 2-methyl-2,3-methylene-6-phthalimidopenam-3-carboxylic acid [mp. 181° to 182°C (dec.)]
45. 2,2,2-Trichloroethyl 2-methyl-2,3-methylene-6-(phenylthio)carbonylaminopenam-3-carboxylate-1-β-oxide (mp. 171.5° to 172.5°C)
46. 2,2,2-Trichloroethyl 2-methyl-2,3-methylene-6-(4-acetamidobenzenesulfonamido)penam-3-carboxylate-1-β-oxide (mp. 149° to 153°C)
47. 2-Methyl-2,3-methylene-6-aminopenam-3-carboxylic acid [mp. 200°C (dec.)]
48. 2-Methyl-2,3-methylene-6(2-phenylglycyl-)aminopenam-3-carboxylic acid, [mp. 200° to 202°C (dec.)]
49. 2,2,2- Trichloroethyl 2-methyl-2,3-methylene-6-(2-phenyl-2-carbamoylhydrazonoacetamido)penam-3-carboxylate [mp. 200° to 201°C (dec.)]
50. 2,2,2-Trichloroethyl 2-methyl-2,3-methylene-6-[1-(4-chlorophenyl)imino-1-acetylthiomethyl-]aminopenam-3-carboxylate, amorphous.
51. Methyl 2-methyl-2,3-methylene-6-(2-phenoxyacetamido)penam-3-carboxylate-1-β-oxide [mp. 153° to 154°C (dec.)]

Reaction of:

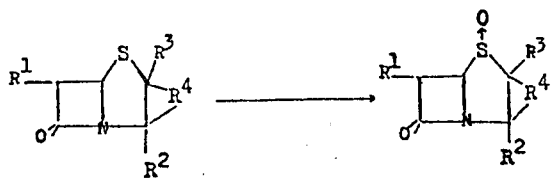

EXAMPLE 1 m-Chloroperbenzoic acid(40 mg.) was added to a solution of 2,2,2-trichloroethyl 2-methyl-2,3-methylene-6-(2-phenylacetamido)penam-3-carboxylate (90 mg) in chloroform(2ml.) under ice-cooling and stirred for an hour. The resultant mixture was washed with a saturated aqueous solution of sodium bicarbonate and water in turn and then dried over magnesium sulfate. The solvent was removed under reduced pressure to give oily 2,2,2-trichloroethyl 2-methyl-2,3-methylene-6-(2-phenylacetamido)penam-3-carboxylate-1-β-oxide (70 mg.). The product was crystallized with ether to give crystals, mp. 148° to 148.5°C.

The following compounds were obtained in similar manners.

1. 2,2,2-Trichloroethyl 2-methyl-2,3-methylene-6-(2-phenylacetamido)penam-3-carboxylate-1-α-oxide [mp. 140° to 143°C. (dec.)]
2. 2,2,2-Trichloroethyl 2-methyl-2,3-methylene-6-aminopenam-3-carboxylate 1-β-oxide p-toluenesulfonate [mp. 176° to 179°C (dec.)]
3. 2,2,2-Trichloroethyl 2-methyl-2,3-methylene-6-[2-(1H-tetrazol-1-yl)-acetamido]penam-3-carboxylate-1-β-oxide [mp. 189° to 192°C (dec.)]
4. 2,2,2-Trichloroethyl 2-methyl-2,3-methylene-6-[2-(2-thienyl)acetamido]-penam-3-carboxylate-1-β-oxide [mp. 118.5 to 122°C (dec.)]
5. 2,2,2-Trichloroethyl 2-methyl-2,3-methylene-6-(3-phenylureido)penam-3-carboxylate-1-β-oxide [(mp. 167.5° to 169.5°C)]
6. 2,2,2-Trichloroethyl 2-methyl-2,3-methylene-6[2-phenyl-2-(2-chlorophenoxy)acetamido]penam-3-carboxylate-1-β-oxide, oil.
7. 2,2,2-Trichloroethyl 2-methyl-2,3-methylene-6(2-phenyl-2-formyloxyacetamido)penam-3-carboxylate-1-β-oxide (mp. 151.5° to 153.5°C)
8. 2,2,2-Trichloroethyl 2-methyl-2,3-methylene-6-[2-(1,3,4-thiadiazol-2-ylthio)acetamido]penam-3-carboxylate-1-β-oxide, oil.
9. 2,2,2-Trichloroethyl -2-methyl-2,3-methylene-6-[2-(5-chloro-1H-benzotriazol-1-yl)acetamido[penam-3-carboxylate-1-β-oxide [mp. 145° to 149°C (dec.)]
10. 2,2,2-Trichloroethyl 2-methyl-2,3-methylene-6-(2-methylthioacetamido)penam-3-carboxylate-1-β-oxide (mp. 177°C)
11. 2,2,2-Trichloroethyl 2-methyl-2,3-methylene-6-[3-(4-chlorophenyl)-thioureido]penam-3-carboxylate-1-β-oxide [mp. 180° to 190°C (dec.)]
12. 2,2,2-Trichloroethyl 2-methyl-2,3-methylene-6-(1-cyclopropylethoxy)carbonylaminopenam-3-carboxylate-1-β-oxide, oil.
13. 2,2,2-Trichloroethyl 2-methyl-2,3-methylene-6-[N-(1-cyclopropylethoxy)-carbonylphenylglycyl-]aminopenam-3-carboxylate-1-β-oxide, foam.
14. 2,2,2-Trichloroethyl 2-methyl-2,3-methylene-6-[3-(2-chlorophenyl)-5-methylisoxazol-4-caboxamido]penam-3-carboxylate-1-β-oxide, amorphous.
15. 2,2,2-Trichloroethyl 2-methyl-2,3-methylene-6-phenyl-glyoxlamidopen-3-carboxylate-1-β-oxide [mp. 175° to 176°C (dec.)]
16. 2,2,2-Trichloroethyl 2-methyl-2,3-methylene-6-(phenylthio)carbonylaminopenam-3-carboxylate-1-β-oxide (mp. 171.5° to 172.5°C)
17. 2,2,2-Trichloroethyl 2-methyl-2,3-methylene-6-(4-acetamidobenzenesulfonamido)penam-3-carboxylate-1-β-oxide (mp. 149° to 153°C)
18. Methyl 2-methyl-2,3-methylene-6-(2-phenoxyacetamido)penam-3-carboxylate-1-β-oxide [mp. 153° to 154°C (dec.)]

Reaction of:

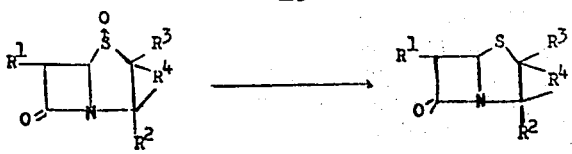

EXAMPLE 1

To a solution of 2,2,2-trichloroethyl 2-methyl-2,3-methylene-6-(2-phenylacetamido)penam-3-carboxylate-1-β-oxide (2.34 g.) in a mixture of anhydrous dimethylformamide (10 ml.) and acetonitrile (20 ml.) were added anhydrous stannous chloride (2 g.) and acetyl chloride (5 ml.) under ice-cooling, and the mixture was stirred for 4 hours at the same temperature. After distilling off the excess acetyl chloride and acetonitrile under reduced pressure, the residue was poured into ice-water containing ethyl acetate and extracted with ethyl acetate. The extract was washed with 3% hydrochloric acid, water, a saturated sodium bicarbonate aqueous solution and water in turn and dried over magnesium sulfate. Crystalline solid (2.02 g.) obtained by distilling off the solvent under reduced pressure was washed with a small amount of ether and dried to give crystals of 2,2,2-trichloroethyl 2-methyl-2,3-methylene-6-(2-phenylacetamido)penam-3-carboxylate (1.23 g.) mp. 140° to 143°C.
Infrared Absorption Spectrum ($CHCl_3$) 3420, 1795, 1745, 1680 $cm^{-1}$

EXAMPLE 2

To a solution of 2,2,2-trichloroethyl -2-methyl-2,3-methylene-6-[2-(1H-tetrazol-1-yl)acetamido]penam-3-carboxylate-1-β-oxide (3.3 g.) in dimethylformamide (17 ml.) was dropwise added phosphorus trichloride (1.7 ml.) under cooling at −10° to −15°C. After stirring for 1 hour, the reaction mixture was poured into a mixture of ethyl acetate (100 ml.) and ice-water (50 ml.), extracted and the aqueous layer was extracted with ethyl acetate (20 ml.). The combined extract was washed with a saturated sodium bicarbonate aqueous solution, a saturated sodium chloride aqueous solution and dried over magnesium sulfate. After drying, the solution was decolorized by activated charcoal and the solvent was distilled off. The residue was crystallized by adding a small quantity of ethanol to give 2,2,2-trichloroethyl 2-methyl-2,3-methylene-6-[2-(1H-tetrazol-1-yl)acetamido]penam-3-carboxylate (2.6 g.), mp. 133° to 137°C.
Analysis for $C_{13}H_{13}N_6O_4SCl_3$ Calc'd: C34.26, H2.87, N18.44 Found: C34.09, H2.56, N18.32
Infrared Absorption Spectrum (Nujol): 3250, 1790, 1740, 1705 $cm^{-1}$

EXAMPLE 3

To a solution of 2,2,2-trichloroethyl 2-methyl-2,3-methylene-6-[2-(2-thienyl)acetamido]penam-3-carboxylate-1-β-oxide (1.94 g.) in dimethylformamide (10 ml.) was dropwise added phosphorus trichloride (1ml.) under cooling at −10° to +15°C, and the mixture was stirred for 1 hour at the same temperature. After the reaction, the reaction mixture was post-treated in the similar manner as described in Example 2 to give 2,2,2-trichloroethyl 2-methyl-2,3-methylene-6-[2-(2-thienyl)acetamido]penum-3-carboxylate (1.34 g.), mp. 144° to 145°C.
Analysis for $C_{16}H_{15}N_2O_4S_2Cl_3$: Calc'd: C40.90, H3.21, N5.98, S13.64, Cl 22.64; Found: C40.92, H,3.07, N5.78, S13.35, Cl 22.42
Infrared Absorption Spectrum (Nujol): 3250, 1790, 1740, 1650 $cm^{-1}$

EXAMPLE 4

To a solution of 2,2,2-trichloroethyl 2-methyl-2,3-methylene-6-(3-phenylureido)penam-3-carboxylate-1-β-oxide (0.96 g.) in dimethylformamide (10 ml.) was dropwise added phosphorus trichloride (0.5 ml.) under cooling at −10° to −15°C, and the mixture was stirred for 1 hour. After the reaction, the reaction mixture was posttreated in a similar manner as described in Example 2 and the obtained crystals were recrystallized from ethanol to give 2,2,2-trichloroethyl 2-methyl-2,3-methylene-6-(3-phenylureido)penam-3-carboxylate(0.61 g.), mp. 153.5° to 155°C.
Infrared Absorption Spectrum (Nujol): 3350, 3250, 1780, 1740, 1710, 1690 $cm^{-1}$

EXAMPLE 5

To a solution of 2,2,2-trichloroethyl 2-methyl-2,3-methylene-6-[2-phenyl-2-(2-chlorophenoxy)acetamido]penam-3-carboxylate-1-β-oxide (2.36 g.) in dimethylformamide (20 ml.) was dropwise added phosphorus trichloride (1 ml.) under cooling at −10° to −15°C, and the mixture was stirred for 1.5 hours. After the reaction, the reaction mixture was poured into a mixture of ethyl acetate (100 ml.) and ice-water (100 ml.), extracted and the ethyl acetate layer was separated. The extract was washed in turn with a sodium bicarbonate aqueous solution, a saturated sodium chloride aqueous solution and dried over magnesium sulfate, after which the solvent was distilled off to give oily 2,2,2-trichloroethyl 2-methyl-2,3-methylene-6-[2-phenyl-2-(2-chlorophenoxy)acetamido]penam-3-carboxylate (1.64 g.).

EXAMPLE 6

To a solution of 2,2,2-trichloroethyl 2-methyl-2,3-methylene-6-(2-phenyl-2-formyloxyacetamido)penam-3-carboxylate-1-β-oxide (0.79 g.) in dimethylformamide (10 ml.) was dropwise added over about 5 minutes a solution of phosphorus trichloride (0.4 ml.) in dimethylformamide (3 ml.) under cooling at −10° to −13°C, and the mixture was stirred for 1 hour. After the reaction, the reaction mixture was post-treated in the similar manner as described in Example 2 and the solvent was distilled off from the ethyl acetate layer to give oily 2,2,2-trichloroethyl 2-methyl-2,3-methylene-6-(2-phenyl-2-formloxyacetamido)penam-3-carboxylate (0.75 g.).
Infrared Absorption Spectrum (Film): 3300, 1790 $cm^{-1}$

EXAMPLE 7

To a solution of 2,2,2-trichloroethyl 2-methyl-2,3-methylene-6-[2-(1,3,4-thiadiazol-2-ylthio)acetamido]penam-3-carboxylate-1-β-oxide (3.54 g.) in dimethylformamide(35 ml.) was dropwise added phosphorus trichloride(1.75 ml.) under cooling at −15°C, and the mixture was stirred for 1 hour. After the reaction, the reaction mixture was post-treated in the similar manner as described in Example 2 and ethyl acetate was distilled off to give oily 2,2,2-trichloroethyl 2-methyl-2,3-methylene-6-[2-(1,3,4-thiadiazol-2-ylthio)acetamido]penam-3-carboxylate(2.7 g.).

EXAMPLE 8

To a solution of 2,2,2-trichloroethyl 2-methyl-2,3-methylene-6-[2-(5-chloro-1H-benzotriazol-1-yl)acetamido]penam-3-carboxylate-1-β-oxide(1.62 g.) in dimethylformamide(15 ml.) was dropwise added phosphorus trichloride(0.8 ml.) under cooling at −15°C, and the mixture was stirred for 1 hour. The reaction mixture was poured into a mixture of ethyl acetate(50 ml.) and ice-water(50 ml.), extracted and the aqueous layer was further extracted with ethyl acetate(15 ml.). The combined ethyl acetate layer was washed in turn with a saturated sodium bicarbonate aqueous solution, a saturated sodium chloride aqueous solution and dried over magnesium sulfate. After drying, the solvent was distilled off under reduced pressure and the residue was crystallized by adding a small amount of ether to give 2,2,2-trichloroethyl 2-methyl-2,3-methylene-6-[2-(5-chloro-1H-benzotriazol-1-yl)acetamido]penam-3-carboxylate(1.0 g.), mp. 164° to 166°C.
Infrared Absorption Spectrum (Nujol): 3250, 1790, 1740, 1680 cm$^{-1}$

EXAMPLE 9

To a solution of 2,2,2-trichloroethyl 2-methyl-2,3-methylene-6-(2-methylthioacetamido)penam-3-carboxylate-1-β-oxide(1.4 g.) in dimethylformamide(14 ml.) was dropwise added phosphorus trichloride (0.75 ml.) under cooling at −20°C, and the mixture was stirred for 1 hour. After stirring, the reaction mixture was poured into a mixture of ethyl acetate(30 ml.) and ice-water(30 ml.), extracted and the aqueous layer was further extracted with ethyl acetate (10 ml.). The combined ethyl acetate layer was washed with a saturated sodium bicarbonate aqueous solution, a saturated sodium chloride aqueous solution in turn and dried over magnesium sulfate. After drying, the solvent was distilled off to give oily 2,2,2-trichloroethyl 2-methyl-2,3-methylene-6-(2-methylthioacetamido)penam-3-carboxylate(1.2 g.).
Infrared Absorption Spectrum (Film): 3270, 1785, 1740, 1660 cm$^{-1}$

EXAMPLE 10

To a solution of 2,2,2-trichloroethyl 2-methyl-2,3-methylene-6-(1-cyclopropylethoxy)carboxylaminopenam-3-carboxylate-1-β-oxide (2.63 g.) in dimethylformamide(15 ml.) was dropwise added phosphorus trichloride(1.5 ml.) under cooling at −10° to −15°C, and the mixture was stirred for 1 hour at the same temperature. After stirring, the reaction mixture was poured into a mixture of ethyl acetate and ice-water, extracted with ethyl acetate and the extract was washed with water, a saturated sodium bicarbonate aqueous solution and water in turn, and dried over magnesium sulfate. After drying, the solvent was distilled off to give oily 2,2,2-trichloroethyl 2-methyl-2,3-methylene-6-(1-cyclopropylethoxy)carbonylaminopenam-3-carboxylate(1.99 g.).
Infrared Absorption Spectrum (Film): 3300, 1795, 1745, 1725, 1715 cm$^{-1}$

EXAMPLE 11

Residue obtained by treating 2,2,2-trichloroethyl 2-methyl-2,3-methylene-6-[N-(1-cyclopropylethoxy)-carbonylphenylglycyl]aminopenam-3-carboxylate-1-β-oxide(4.92 g.) in the similar manner as described in Example 10 was washed with a mixture of ether and petroleum ether and dried to give amorphous 2,2,2-trichloroethyl 2-methyl-2,3-methylene-6-[N-(1-cyclopropylethoxy)carbonylphenylglycyl]aminopenam-3-carboxylate(3.66 g.)
Infrared Absorption Spectrum (Nujol): 3300, 1790, 1745, 1708, 1670 cm$^{-1}$

EXAMPLE 12

By treating 2,2,2-trichloroethyl 2-methyl-2,3-methylene-6[3-(2-chlorophenyl)-5-methylisoxazol-4-carboxamido]penam-3-carboxylate-1-β-oxide(3.55 g.) in the similar manner as described in Example 10, there was obtained foamy 2,2,2-trichloroethyl 2-methyl-2,3-methylene-6-[3-(2-chlorophenyl)-5-methylisoxazol-4-carboxamido]penam-3-carboxylate (2.88 g.).
Infrared Absorption Spectrum (Nujol) 3350, 1795, 1746, 1670 cm$^{-1}$

EXAMPLE 13

A reaction mixture obtained by treating 2,2,2-trichloroethyl 2-methyl-2,3-methylene-6-phenyglyoxylamidopenam-3-carboxylate-1-β-oxide(3.95 g.) in the similar manner as described in Example 10 was poured into ice-water and precipitating crystals were collected by filtration to give 2,2,2-trichloroethyl 2-methyl-2,3-methylene-6-phenylglyoxylamidopenam-3-carboxylate(3.80 g.), mp. 132° to 133°C.
Infrared Absorption Spectrum (Nujol): 3270, 1785, 1745, 1679 cm$^{-1}$

EXAMPLE 14

To a solution of 2,2,2-trichloroethyl 2-methyl-2,3-methylene-6-(phenylthio)carbonylaminopenam-3-carboxylate-1-β-oxide(2.8 g.) in dried dimethylformamide(28 ml.) was dropwise added phosphorus trichloride(1.5 ml.) under cooling at −10° to −13°C, and the mixture was stirred for 1 hour. After the reaction, the reaction mixture was poured into a mixture of ethyl acetate(50 ml.) and ice-water (50 ml.), extracted and the aqueous layer was further extracted with ethyl acetate(20 ml.). The combined extact was washed with a saturated sodium bicarbonate aqueous solution, a sodium chloride aqueous solution in turn and dried over magnesium sulfate. After drying, the solvent was distilled off under reduced pressure and the residue was crystallized by adding a small amount of ethanol to give 2.2.2-trichloroethyl 2-methyl-2,3-methylene-6-phenylthio)carbonylaminopenam-3-carboxylate(1.63 g.), mp. 121°C.
Analysis for $C_{17}H_{15}N_2O_4S_2Cl_3$: Calc'd: C42.38, H3.14, N5.82: Found: C42.67, H3.07, N5.71
Infrared Absorption Spectrum (Nujol): 3300, 1780, 1740, 1690 cm$^{-1}$

EXAMPLE 15

2,2,2-Trichloroethyl 2-methyl-2,3-methylene-6-(4-acetamidobenzenesulfonamido)penam-3-carboxylate-1-β-oxide(1.7 g.) was treated using phosphorus trichloride(0.75 g.) in the similar manner as described in Example 10 and the residue was recrystallized from a small amount of ethanol to give 2,2,2-trichloroethyl 2-methyl-2,3-methylene-6-(4-acetamidobenzenesulfonamido)penam-3-carboxylate (1.03 g.), mp. 193° to 198°C.
Analysis for $C_{18}H_{18}O_6N_3S_2Cl_3$: Calc'd: C39.82, H3.36, N7.74; Found: C39.74, H3.23, N7.66

Infrared Absorption Spectrum (Nujol): 3350, 3150, 1800, 1760, 1680 cm$^{-1}$

EXAMPLE 16:

To a solution of 2,2,2-trichloroethyl 2-methyl-2,3-methylene-6-(benzyloxycarboxamido)penam-3-carboxylate-1-β-oxide(1.1g.) in dimethylformamide(10 ml.) was dropwise added phosphorus trichloride (1.1 ml.) under stirring and cooling at −15°C, and the mixture was stirred for 1 hour at the same temperature. After the reaction, the reaction mixture was poured into a mixture of water(30 ml.) and ethyl acetate(30 ml) and the ethyl acetate layer was washed several times with 5% sodium bicarbonate aqueous solution and water in turn and thereafter dried. After drying, the solvent was distilled off to give oily 2,2,2-trichloroethyl 2-methyl-2,3-methylene-6-(benzyloxycarboxamido)penam-3-carboxylate(0.8 g.).
Infrared Absorption Spectrum (Film): 3270, 1790, 1740, 1729, 1660 cm$^{-1}$

EXAMPLE 17

To a solution of 2,2,2-trichloroethyl 2-methyl-2,3-methylene-6-(2-phenoxyacetamido)penam-3-carboxylate-1-β-oxide(3.00 g.) in dimethylformamide(30 ml.) was dropwise added phosphorus trichloride (1.50 ml.) under stirring and cooling at −10° to −15°C, and the mixture was stirred for 1 hour. After the reaction, the reaction mixture was poured into a mixture of ethyl acetate(60 ml.) and ice-water(30 ml.) and then the aqueous layer was further extracted twice with ethyl acetate, after which the ethyl acetate layers were combined. The extract was washed with a saturated sodium bicarbonate aqueous solution and a saturated sodium chloride aqueous solution in turn and then dried over magnesium sulfate. After drying, the solvent was distilled off and the residue was crystallized with ethanol, after which the crystals were washed with a mixture of ether and isopropylether to give 2,2,2-trichloroethyl 2-methyl-2,3-methylene-6-(2-phenoxyacetamido)penam-3-carboxylate(1.50 g.), mp. 94° to 97°C.

EXAMPLE 18

To a solution of methyl 2-methyl-2,3-methylene-6-(2-phenoxyacetamido)penam-3-carboxylate-1-β-oxide(2.26 g.) in anhydrous dimethylformamide(33 ml.) was dripwise added over a 5 minutes period phosphorus trichloride(2.35 g.) under stirring and cooling at −15°C, and the mixture was stirred for 45 minutes at the same temperature. After the reaction, the reaction mixture was poured into a mixture of ethyl acetate(60 ml.) and ice-water(60 ml.) containing sodium chloride, and the aqueous layer was further extracted twice with ethyl acetate, after which the ethyl acetate layers were combined. The extract was washed twice with a saturated sodium chloride aqueous solution with a dilute sodium bicarbonate aqueous solution four times and with a saturated sodium chloride aqueous solution once in turn and then dried over magnesium sulfate. After drying, the solvent was removed to give pale-yellow oil of methyl 2-methyl-2,3-methylene-6-(2-phenoxyacetamido)penam-3-carboxylate(2.2 g.).
Infrared Absorption Spectrum (Chloroform) 3400, 1790, 1728, 1690 cm$^{-1}$

EXAMPLE 19

To a solution of 2,2,2-trichloroethyl 2-methyl-2,3-methylene-6-[2(3-chlorophenyl)acetamido]penam-3-carboxylate-1-β-oxide(5.13 g.) in dimethylformamide(50 ml.) was dropwise added phosphorus trichloride (2.5 ml.) under stirring and cooling at −15°C, and the mixture was stirred for 1 hour at the same temperature. After the reaction, the reaction mixture was poured into a mixture of ethyl acetate(100 ml.) and water (150 ml.) and the ethyl acetate layer was washed with a 5% sodium bicarbonate aqueous solution and water in turn and then dried over magnesium sulfate. After drying, the oily residue obtained by distilling off the solvent was dissolved in ethanol and allowed to stand to give 2,2,2-trichloroethyl 2-methyl-2,3-methylene-6[2-(3-chlorophenyl)acetamido]penam-3-carboxylate(3.8 g.), mp. 123°C.

EXAMPLE 20

To a solution of 2,2,2-trichloroethyl 2-methyl-2,3-methylene-6-[2(1,2,5-thiadiazol-3-yl)acetamido]penam-3-carboxylate-1-β-oxide (19 g.) in anhydrous dimethylformamide (200 ml.) was dropwise added phosphorus trichloride(10 ml.) under stirring and cooling at −13 to −15°C, and the mixture was stirred for 1 hour. After the reaction, the reaction mixture was poured into a mixture of ethyl acetate (500 ml.) and ice-water(500 ml.) and the aqueous layer was further extracted with ethyl acetate(200 ml.), after which the ethyl acetate layers were combined. The extract was washed twice with a saturated sodium bicarbonate aqueous solution(200 ml.) and once with a saturated sodium chloride aqueous solution in turn and then dried over magnesium sulfate. After drying, the solvent was removed under reduced pressure and volatile substance was completely removed under reduced pressure to give 2,2,2-trichloroethyl 2-methyl-2,3-methylene-6-[2-(1,2,5-thiadiazol-3-yl)acetamido]penam-3-carboxylate (17.5 g.), mp. 160° to 167°C (dec.).

EXAMPLE 21

To a solution of 2,2,2-trichloroethyl 2-methyl-2,3-methylene-6(2-sulfophenylacetamido)penam-3-carboxylate-1-β-oxide (0.20 g.) in anhydrous dimethylformamide (5 ml.) was added phosphorus trichloride (0.12 ml.) under cooling at −10 to −15°C and then stirred at the same temperature for 30 minutes. The resultant mixture was poured into ice-water and extracted three times with ethyl acetate. The extract was washed with a saturated aqueous solution of sodium chloride, dried and then concentrated to give oily product of 2,2,2-trichloroethyl 2-methyl-2,3-methylene-6-(2-sulfophenylacetamido) penam-3-carboxylate (160 mg.) Infrared Absorption Spectrum (film) 3230, 1790, 1740, 1650 cm$^{-1}$.

The following compounds were obtained by using the same procedure as those of Examples 1 to 20.
1. 2-Methyl-2,3-methylene-6-(2-phenylacetamido)penam-3-carboxylic acid, mp. 112° to 118°C (dec.).
2. 2-Methyl-2,3-methylene-6-[2-(1H-tetrazol-1-yl)acetamido]penam-3-carboxylic acid, mp. 167° to 170°C (dec.).
3. 2-Methyl-2,3-methylene-6-[2-(2-thienyl)acetamido]penam-3-carboxylic acid. m.p. 106° to 108°C (dec.)].
4. 2-Methyl-2,3-methylene-6-(3-phenylureido)penam-3-carboxylic acid, mp. 108° to 110°C(dec.)].
5. N,N'-Dibenzylethylenediamine salt of 2-methyl-2,3-methylene-6-[2-phenyl-2-(2chlorophenoxy)acetamido]penam-3-carboxylic acid, mp. 107° to 110°C (dec.)].

6. 2-Methyl-2,3-methylene-6-(2-phenyl-2-formyloxyacetamido)penam-3-carboxylic acid (oil).
7. Sodium 2-methyl-2,3-methylene-6-[1,3,4-thiadiazol-2-ylthio)-acetamido]penam-3-carboxylate, mp. 171° to 177°C (dec.)
8. Sodium 2-methyl-2,3-methylene-6-(2-methylthioacetamido)penam-3-carboxylate, mp. 178° to 181°C (dec.).
9. N,N'-Dibenzylethylenediamine salt of 2-methyl-2,3-methylene-6-(1-cyclopropylethoxy)carbonylaminopenam-3-carboxylic acid, mp. 148° to 149.5°C (dec.).
10. 2-Methyl-2,3-methylene-6[N-(1-cyclopropylethoxy)phenylglycyl]-aminopenam-3-carboxylic acid (amorphous).
11. N,N'-Dibenzylethylenediamine salt of 2-methyl-2,3-methylene-6[3-(2-chlorophenyl)-5-methylisoxazol-4-carboxamido]penam-3-carboxylic acid, mp. 97° to 100°C. (dec.).
12. Sodium 2-methyl-2,3-methylene-6-(2-hydroxy-2-phenylacetamido)penam-3-carboxylate, mp. 180° to 190°C.(dec.).
13. 2-Methyl-2,3-methylene-6-(2-phenyl-2-carbamoylhydrazonoacetamido)penam-3-carboxylic acid, mp. 198° to 199°C (dec.).
14. 2-Methyl-2,3-methylene-6-[1-(4-chlorophenyl)imino-1-acetylthiomethyl]aminopenam-3-carboxylic acid, mp. 147° to 150°C (dec.).
15. 2-Methyl-2,3-methylene-6-(phenylthio)carbonylaminopenam-3-carboxylic acid, mp. 116° to 119°C(dec.)
16. 2-Methyl-2,3-methylene-6(4-acetamidobenzenesulfonamido)penam-3-carboxylic acid, mp. 230°C (dec.).
17. N,N'-Dibenzylethylenediamine salt of 2-methyl-2,3-methylene-6-phthalimidopenam-3-carboxylic acid, mp. 181° to 182°C (dec.).
18. 2-Methyl-2,3-methylene-6-aminopenam-3-carboxylic acid, mp. 200°C (dec.).
19. 2-Methyl-2,3-methylene-6-(2-phenylglycyl)aminopenam-3-carboxylic acid, mp. 200° to 202°C (dec.).
20. 2,2,2-Trichloroethyl 2-methyl-2,3-methlene-6-(2-phenyl-2-semicarbazonoacetamido)penam-3-carboxylate, mp. 200° to 201°C (dec.).
21. 2,2,2-Trichloroethyl 2-methyl-2,3-methylene-6-[1-(4-chlorophenyl)imino-1-acetylthiomethyl-]aminopenam-3-carboxylate(amorphous).

Reaction of:

EXAMPLE 1

A solution of 2-methyl-2,3-methylene-6-(1-cyclopropylethoxy)carbonylaminopenam-3-carboxylic acid(840 mg.) in formic acid(5 ml.) was stirred for 1.5 hours at room temperature. After the reaction, formic acid was distilled off under reduced pressure. The residue was washed with ether, crystallized by adding acetonitrile containing water and the crystals were collected by filtration to give 2-methyl-2,3-methylene-6-aminopenam-3-carboxylic acid(380 mg.), mp. 200°C (dec.).

Infrared absorption Spectrum (Nujol): 1788, 1608 cm$^{-1}$

EXAMPLE 2

To a solution of 2,2,2-trichloroethyl 2-methyl-2,3-methylene-6-(2-phenylacetamido)penam-3-carboxylate(0.46 g.) in dried benzene (10 ml.) were added pyridine(0.12 g.) and phosphorus pentachloride (0.30 g.) in turn, and the mixture was stirred for 2 hours at room temperature. Anhydrous methanol(1 ml.) was added to the solution under cooling at −10°C and the solution was stirred for 2 hours. To the solution was added water(5 ml.) at 10°C, and the solution was further stirred for 10 minutes. After the reaction was completed, aqueous layer was separated from the reaction mixture, adjusted to pH 8 to 9 by a sodium bicarbonate aqueous solution and extracted with ethyl acetate. The extract was dried over magnesium sulfate and the solvent was distilled off under reduced pressure. The residue was washed with a small amount of petroleum ether and dissolved in a small quantity of ethyl acetate. A solution of p-toluenesulfonic acid monohydrate in ethyl acetate was added to the solution and precipitates were collected by filtration and thereafter dried to give 2,2,2-trichloroethyl 2-methyl-2,3-methylene-6-aminopenam-3-carboxylate p-toluenesulfonate(25 mg.), mp. 179° to 180°C(dec.).

Infrared Absorption Spectrum (Nujol): 1800, 1755 cm$^{-1}$.

EXAMPLE 3

To a solution of 2,2,2-trichloroethyl 2-methyl-2,3-methylene-6-(2-phenylacetamido)penam-3-carboxylate-1-β-oxide(960 mg.) in dried dichloromethane(10 ml.) were added dimethylaniline(370 mg.) and phosphorus pentachloride (620 mg.) in turn under cooling at −40°C. The mixture was stirred for 2 hours at −30° to −40°C and further stirred for 30 minutes at −10 to −20°C. The solution was cooled at −30° to −40°C and anhydrous methanol(0.7 ml.) was added dropwise to the solution and then the mixture was stirred for 2 hours at −20° to −30°C. Water(0.7 ml.) was added to the reaction mixture and the solution was stirred for 1 hour under ice-cooling. Water (5 to 6 ml.) was added the mixture and aqueous layer was separated. The aqueous layer was neutralized by a sodium bicarbonate aqueous solution and extracted with ethyl acetate. The extract was washed with water, dried over magnesium sulfate and the solvent was distilled off under reduced pressure. The oily residue was washed with a small amount of petroleum ether and dissolved in a small quantity of ethyl acetate. And then a solution of p-toluenesulfonic acid monohydrate(120 mg.) in ethyl acetate(5 ml.) was added to the solution. Precipitates were collected by filtration and fractionally crystallized from acetone to give 2,2,2-trichloroethyl 2-methyl-2,3-methylene-6-aminopenam-3-carboxylate-1-β-oxide p-toluenesulfonate(60 mg.), mp. 176° to 179°C (dec.).

Infrared Absorption Spectrum (Nujol): 1800, 1745 cm$^{-1}$.

Example 4

To a solution of 2,2,2-trichloroethyl 2-methyl-2,3-methylene-6-(2-benzyloxycarboxamido)penam-3-carboxylate(0.8 g.) in tetrahydrofuran(70 ml.) was added 10% palladium on carbon(1.5 g.) and the starting compound was subjected to catalytic reduction for 3 hours at room temperature. After the reaction, the reaction mixture was filtered and the filtrate was concentrated under reduced pressure, after which the residue was dissolved in ethyl acetate (2 ml.). To this solution was added a solution of p-toluenesulfonic acid in ethyl acetate and precipitating crystals were collected by filtration, washed with ether and dried to give 2,2,2-trichloroethyl 2-methyl-2,3-methylene-6-aminopenam-3-carboxylate p-toluenesulfonate (0.43 g.), mp. 179° to 180°C (dec.). 2,2,2-Trichloroethyl 2-methyl-2,3-methylene-6-aminopenam-3-carboxylate p-toluenesulfonate[mp. 179° to 180°C (dec.)] was obtained according to similar manners to those of Examples 2 to 4 in which each of the following compounds were used as the starting compound.

a. 2,2,2-trichloroethyl 2-methyl-2,3-methylene-6-[2-(1H-tetrazol-1-yl)acetamido]penam-3-carboxylate (mp. 133° to 137°C)
b. 2,2,2-trichloroethyl 2-methyl-2,3-methylene-6-[2-(2-thienyl)acetamido]penam-3-carboxylate (mp. 144° to 145°C)
c. 2,2,2-trichloroethyl 2-methyl-2,3-methylene-6-[2-phenyl-2-(2-chlorophenoxy)acetamido]penam-3-carboxylate (oil)
d. 2,2,2-trichloroethyl 2-methyl-2,3-methylene-6-(2-phenyl-2-formyloxyacetamido)penam-3-carboxylate (oil)
e. 2,2,2-trichloroethyl 2-methyl-2,3-methylene-6-[2-(1,3,4-thiadiazol-2-ylthio)acetamido]penam-3-carboxylate (oil)
f. 2,2,2-trichloroethyl 2-methyl-2,3-methylene-6-[2-(5-chloro-1H benzotriazol-1-yl)acetamido]penam-3-carboxylate (mp. 164° to 166°C)
g. 2,2,2-trichloroethyl 2-methyl-2,3-methylene-6-(2-methylthioacetamido)penam-3-carboxylate (oil)
h. 2,2,2-trichloroethyl 2-methyl-2,3-methylene-6-[N-(1-cyclopropylethoxy)carbonylphenylglycyl]aminopenam-3-carboxylate (amorphous)
i. 2,2,2-trichloroethyl 2-methyl-2,3-methylene-6-[3-(2-chlorophenyl)-5-methylisoxazol-4-carboxamido]penam-3-carboxylate (foam)
j. 2,2,2-trichloroethyl 2-methyl-2,3-methylene-6-(2-phenyl-2-semicarbazonoacetamido)penam-3-carboxylate [mp. 200° to 201°C (dec.)]
k. 2,2,2-trichloroethyl 2-methyl-2,3-methylene-6-[2-(1H-tetrazol-1-yl)acetamido]penam-3-carboxylate-1-β-oxide [mp. 189° to 192°C (dec.)]
l. 2,2,2-trichloroethyl 2-methyl-2,3-methylene-6-[2-(2-thienyl)acetamido]penam-3-carboxylate-1-β-oxide [mp. 118.5° to 122°C (dec.)]
m. 2,2,2-trichloroethyl 2-methyl-2,3-methylene-6-[2-phenyl-2-(2-chlorophenoxy)acetamido]penam-3-carboxylate-1-β-oxide (oil)
n. 2,2,2-trichloroethyl 2-methyl-2,3-methylene-6-(2-phenyl-2-formyloxyacetamodo)penam-3-carboxylate-1-β-oxide [mp. 151.5 to 153.5°C (dec.)]
o. 2,2,2-trichloroethyl 2-methyl-2,3-methylene-6-[2-(1,3,4-thiadiazol-2-ylthio)acetamido]penam-3-carboxylate-1-β-oxide (oil)
p. 2,2,2-trichloroethyl 2-methyl-2,3-methylene-6-[2-(5-chloro-1H-benzotriazol-1-yl)acetamido]penam-3-carboxylate-1-β-oxide [mp. 145° to 149°C (dec.)]
q. 2,2,2-trichloroethyl 2-methyl-2,3-methylene-6-(2-methylthioacetamido)penam-3-carboxylate-1-β-oxide (mp. 177°c)
r. 2,2,2-trichloroethyl 2-methyl-2,3-methylene-6-(1-cyclopropylethoxy)carbonylaminopenam-3-carboxylate-1-β-oxide (oil)
s. 2,2,2-trichloroethyl 2-methyl-2,3-methylene-6-[N-(1-cyclopropylethoxy)carbonylphenylglycyl]aminopenam-3-carboxylate-1-β-oxide (foam)
t. 2,2,2-trichloroethyl 2-methyl-2,3-methylene-6-[3-(2-chlorophenyl)-5-methylisoxazol-4-carboxamido]penam-3-carboxylate-1-β-oxide (amorphous) Reaction of:

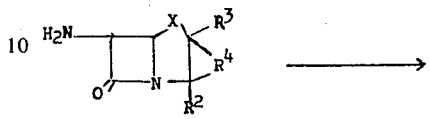

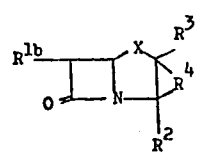

EXAMPLE 1

To a solution of pivaloyl chloride (1.45 g.) in dried metylene chloride (30 ml.) was added a solution of 1H-tetrazol-1-acetic acid (1.35 g.), triethylamine(1.2 g.), N,N-dimethyl-benzylamine(5 drops) and dried methylene chloride (30 ml.) under cooling at −10 to −15°C over 10 minutes. After stirring for 1 hour at the same temperature, to the solution was dropwise added at −10 to −15°C a solution of 2,2,2-trichloethyl2-methyl-2,3-methylene-6-aminopenam-3-carboxylate-1-β-oxide p-toluenesulfonate (5.3 g.), triethylamine (1 g.) and dried methylene chloride (30 ml.) and then stirred for 3 hours. After the reaction crystals precipitated were collected by filtration and washed with methylene chloride layer was washed with 2 % hydrochloric acid, a saturated aqueous solution of sodium bicarbonate and water in turn and then dried over magnesium sulfate. The solvent was removed and the residue was crystallized by adding a small amount of ethanol. The crystals were combined to give 2,2,2-trichloroethyl 2-methyl-2,3-methylene-6-[2-(1H-tetrazol-1-yl)acetamido]penam-3-carboxylate-1-β-oxide (3.65 g.), mp. 189 to 192°C (dec.).

EXAMPLE 2

To a mixture of toluenesulfonate (3.2 g.) of 2,2,2-trichloroethyl 2-methyl-2,3-methylene-6-aminopenam-3-carboxylate-1-β-oxide toluensulfonate (3.2 g.) and dried methylene chloride (30 ml.) was added triethylamine (1.3 g.) under cooling at −10 to −15°C and the mixture was dissolved with stirring. To the solution was added a solution of 2-thienylacetyl chloride (1.14 g.) in methylene chloride (5 ml.), and the reaction mixture was stirred for 3 hours at the same temperature. The reaction mixture was washed with 2% hydrochloric acid, aqueous solution of sodium bicarbonate and water in turn, and the residue was crystallized by adding ether to give 2,2,2-trichloroethyl 2-methyl-2,3-methylene-6-[2-(2-thienyl)acetamido]penam-3-carboxylate-1-β-oxide (2.44 g.), mp 118.5 to 122°C (dec.).

EXAMPLE 3

To 3 a suspension of 2,2,2-trichloroethyl 2-methyl-2,3-methylene-6-aminopenam-3-carboxylate-1-β-oxide p-toluenesulfonate (2.12 g.) in dried methylene chloride (20 ml.) was added triethylamine (0.4 g.) under ice-cooling. To the solution was dropwise added phenyl isocyanate (0.54 g.), and the reaction mixture was stirred at the same temperature for 1.5 hours. After the reaction, the reaction mixture was washed with 2% hydrochloric acid, aqueous solution of sodium bicarbonate, water and ether in turn, and then dried to give 2,2,2-trichloroethyl 2-methyl-2,3-methylene-6-(3-phenylureido)penam-3-carboxylate-1-β-oxide (1.85 g.), mp. 167.5° to 169.5°C.

EXAMPLE 4

To a suspension of toluenesulfonate (2.67 g.) of 2,2,2-trichloroethyl 2-methyl-2,3-methylene-6-aminopenam-3-carboxylate-1-β-oxide toluenesulfonate (2.67 g.) in dried methylene chloride (30 ml.) was added triethylamine under cooling at −10°C. To the solution was dropwise added over about 5 minutes a solution of 2-(2-chlorophenoxy)-dl-acetic acid, which was prepared by reacting 2-phenyl-2-(2-chlorophenoxy)-dl-acetic acid (1.6 g.) with thionyl chloride (5 ml.) in methylene chloride (10 ml.), over about 5 minutes, and the reaction mixture was stirred at the same temperature for 2 hours. After the reaction, the reaction mixture was washed with 2% hydrochloric acid, an aqueous solution of sodium bicarbonate and water, and then dried to give oily 2,2,2-trichloroethyl 2-methyl-2,3-methylene-6-[2-phenyl-2-(2-chlorophenoxy)acetoamido]penam-3-carboxylate-1-β-oxide (2.63 g.).
Infrared Absorption Spectrum (Liquid film): 3350, 1800, 1790, 1750 cm$^{-1}$

EXAMPLE 5

To a solution of 2,2,2-trichloroethyl 2-methyl-2,3-methylene-6-aminopenam-3-carboxylate-1-β-oxide p-toluenesulfonate (1.06 g.) in dried tetrahydrofuran (20 ml.) was added o-formylmandelic acid (0.36 g.) with stirring. To the solution were added triethylamine (0.2 g.) and dicyclohexylcarbodiimide (500 mg.) in turn under ice-cooling with stirring and further stirred for 1 hour at the same temperature. After stirring at 10°C for 2 hours, the precipitates were filtered off and the filtrate was concentrated under reduced pressure. The residue was dissolved in ethyl acetate (30 ml.). The ethyl acetate solution was washed with water, saturated aqueous solution of sodium bicarbonate and a saturated aqueous solution of sodium chloride in turn, and dried over magnesium sulfate. The solution was concentrated under reduced pressure and crystallized by adding a small amount of ether to give 2,2,2-trichloroethyl 2-methyl-2,3-methylene-6-(2-phenyl-2-formyloxyacetoamido)penam-3-carboxlate-1-β-odixe (0.68 g.), mp. 151.5° to 153.5°C.

EXAMPLE 6

To a solution of pivaloyl chloride (0.58 g.) in dried methylene chloride (10 ml.) was a solution of 2-[(1,3,4-thiadiazol-2-yl)thio]-acetic acid (0.85 g.), triethylamine (0.48 g.) and N,N-dimethylbenzylamine (1 drop) in dried methylene chloride (10 ml.) under cooling at −10°C. After stirring for 1 hour at the same temperature, to the solution was added under cooling at −10° to −15°C a solution of 2,2,2-trichloroethyl 2-methyl-2,3-methylene 6-aminopenam-3-carboxylate-1-β-oxide p-toluenesulfonate(2.14 g.) and triethylamine (0.4 g.) in dried methylene chloride, and further stirred for 2.5 hours. After the reaction, the reaction mixture was washed with 2% hydrochloric acid, an aqueous solution of sodium bicarbonate and water in turn, and then dried methylene chloride, and further stirred for 2.5 hours. After the reaction, the reaction mixture was washed with 2% hydrochloric acid, an aqueous solution of sodium bicarbonate and water in turn, and then dried to give oily 2,2,2-trichloroethyl 2-methyl-2,3-methylene-6-[2-(1,3,4-thiadiazol-2-ylthio)acetoamido]penam-3-carboxylate-1-β-oxide (1.72 g.).
Infrared Absorption Spectrum (Liquid film): 3300, 1785, 1740, 1670 cm$^{-1}$

EXAMPLE 7

To a solution of pivaloyl chloride (0.58 g.) in dried methylene chloride (10 ml.) was added a solution of 5-chloro-1H-benzotriazol-1-acetic acid (1.01 g.), triethyamine (0.48 g.) and N,N-dimethylbenzylamine (2 drops) in dried methylene chloride under cooling at −10°C, and further stirred for an hour. To the solution was added under cooling at −10° to −15°C a solution of 2,2,2-trichloroethyl 2-methyl-2,3-methylene-6-aminopenam-3-carboxylate-1-β-oxide p-toluenesulfonate (2.2 g.) and triethylamine (0.4 g.) in dried methylene chloride, and then the reaction mixture was stirred for 2.5 hours. After the reaction, the reaction mixture was washed with water, 2% hydrochloric acid, a saturated aqueous solution of sodium bicarbonate and a saturated aqueous solution of sodium chloride in turn and then dried over magnesium sulfate. The solvent was removed off from the reaction mixture under reduced pressure and the residue was crystallized by adding a small amount of ether to give 2,2,2-trichloroethyl 2-methyl-2,3-methylene-6-[2-(5-chloro-1H-benzotriazol-1-yl)acetoamido]penam-3-carboxylate-1-β-oxide(1.9 g.), mp. 145° to 149°C.

EXAMPLE 8

To a solution of ethyl chloroformate (0.78 g.) in dried methylene chloride (10 ml.) was added a solution of methylthioacetic acid (0.76 g.), triethylamine (0.72 g.) and N,N-dimethylbenzylamine (2 drops) in dried methylene chloride (10 ml.) under cooling at −10°C. After stirring for an hour, to the solution was dropwise added a solution of 2,2,2-trichloroethyl 2-methyl-2,3-methylene-6-aminopenam-3-carboxylate-1-β-oxide p-toluenesulfonate (3.2 g.) and triethylamine (0.6 g.) in absolute methylene chloride (10 ml.), and then the reaction mixture was stirred for 2.5 hours. After the reaction, the reaction mixture was washed with 2% hydrochloric acid, a saturated aqueous solution of sodium bicarbonate and a saturated aqueous solution of sodium chloride in turn and then dried dried over magnesium sulfate. The solvent was removed off from the reaction mixture under reduced pressure and the residue was crystallized by adding a small amount of ether to give 2,2,2-trichloroethyl 2-methyl-2,3-methylene-6-(2-methylthioacetoamido)penam-3-carboxylate-1-β-oxide (2.38 g.), mp. 177°C.

EXAMPLE 9

To a suspension of 2,2,2-trichloroethyl 2-methyl-2,3-methylene-6-aminopenam-3-carboxylate-1-β-oxide p-toluenesulfonate (4.32 g.) in dried methylene chloride (50 ml.) was added triethylamine (0.81 g.). To the solution was added 4-chlorophenylisothiocyanate (1.36 g.) under ice-cooling and stirred at the same temperature for 45 minutes and then at room temperature for additional 2 hours. Crystals precipitated were collected by filtration and washed with chloroform. The filtrate and the washing solution were combined together and washed with dilute hydrochloric acid, water, a saturated aqueous solution of sodium bicarbonate and water and then dried over magnesium sulfate. After the solvent was removed off under reduced pressure, the crystals were washed with ether. The crystals and the above-obtained crystals were combined together to give 2,2,2-trichloroethyl 2-methyl-2,3-methylene-6-[3-(4-chlorophenyl)thioureido]penam-3-carboxylate-1-β-oxide (3.63 g.), mp. 180° to 190°C (dec.).

EXAMPLE 10

To a solution of phosgene (1.1 g.) in tetrahydrofuran (10 ml.) was added 1-cyclopropylethanol (940 mg.) under cooling at −10° to −112°C and stirred for 1.5 hours at th same temperature. To the solution containing (1-cyclopropyl)ethoxycarbonylchloride was added under cooling at −5° to −10°C a solution of 2,2,2-trichloroethyl 2-methyl-2,3-methylene-6-aminopenam-3-carboxylate-1-β-oxide p-toluenesulfonate (4.32 g.) and triethylamine (3.03 g.) in tetrahydrofuran (20 ml.) and then stirred at −10° to −15°C for 2 hours. Tetrahydrofuran was removed under reduced pressure at room temperature and to the residue was added water, and then extracted with ethyl acetate. The extract was washed with dilute phosphoric acid, water, a saturated aqueous solution of sodium bicarbonate and water, and then dried over magnesium sulfate. The solvent was removed under reduced pressure to give oily 2,2,2-trichloroethyl 2-methyl-2,3-methylene-6-(1-cyclopropylethoxy)carbonylaminopenam-3-carboxylate-1-β-oxide (3.35 g.).
Infrared Absorption Spectrum: 3350, 1792, 1750, 1712, 1680 cm$^{-1}$

EXAMPLE 11

To a solution of ethyl chloroformate (1.04 g.) in methylene chloride (30 ml.) was added a solution of N-(1-cyclohexylethoxycarbonyl)-phenylglycine (2.60 g.), N,N-dimethylbenzylamine (5 drops) and triethylamine (960 mg.) in methylene chloride (20 ml.) under cooling at −17° to −20°C and the solution was stirred at same temperature for 1.5 hours. To the solution was added a solution of 2,2,2-trichloroethyl 2-methyl-2,3-methylene-6-aminopenam-3-carboxylate-1-β-oxide p-toluenesulfonate (4.28 g.) and triethylamine (820 mg.) in methylene chloride (30 ml.) at −17° to −20°C and then stirred at same temperature for an hour. After the reaction, the reaction mixture was poured into ice-water and the methylene chloride layer was separated. The aqueous layer was extracted with chloroform and the chloroform extract combined with the methylene chloride layer. The extract was washed with dilute phosphoric acid, water, a saturated aqueous solution of sodium bicarbonate and water in turn, and then dried over magnesium sulfate. The solvent was removed under reduced pressure to give foamy 2,2,2-trichloroethyl 2-methyl-2,3-methylene-6-[N-(1-cyclopropylethoxy)carbonyphenylglycyl]aminopenam-3-carboxylate-1-β-oxide (5.10 g.).
Infrared Absorption Spectrum (Nujol): 3300, 1795, 1750, 1705, 1685 cm$^{-1}$

EXAMPLE 12

To a suspension of 2,2,2-trichloroethyl 2-methyl-2,3-methylene-6-aminopenam-3-carboxylate-1-β-oxide p-toluenesulfonate (3.21 g.) in dried methylene chloride (30 ml.) was added triethylamine (1.31 g.) under cooling at −12° to −14°C. To the solution was dropwise added under cooling at −12° to −14°C a solution of 3-(2-chlorophenyl)-5-methylisoxazol-4-carbonyl chloride, which was prepared from 3-(2-chlorophenyl)-5-methylisoxazol-4-carboxylic acid (1.78 g.) and thionyl chloride (10 ml.), in methylene chloride and then stirred for 5 hours. After the reaction, to the solution was added ice-water, and the resulant mixture was washed with water, dilute phosphoric acid, an aqueous solution of sodium bicarbonate and water in turn, and dried over magnesium sulfate. The solvent was removed under reduced pressure to give amorphous crystals of 2,2,2-trichloroethyl 2-methyl-2,3-methylene-6-[3-(2-chlorophenyl)-5-methylisoxazol-4-carbonamido]penam-3-carboxylate-1-β-oxide (3.83 g.).
Infrared Absorption Spectrum (CHCl$_3$): 3390, 1800, 1751, 1669 cm$^{-1}$

EXAMPLE 13

2,2,2-trichloroethyl 2-methyl-2,3-methylene-6-phenylglyoxylamido-penam-3-carboxylate-1-β-oxide (830 mg.), mp 175° to 176°C was obtained by treating in the similar manner as described in Example 11 using 2,2,2-trichloroethyl 2-methyl-2,3-methylene-6-aminopenam-3-carboxylate-1-β-oxide p-toluenesulfonate (1.08 g.) and a mixed anhydride, which was prepared from phenylglyoxyl acid and ethyl carbonate.

EXAMPLE 14

Sodium carbonate (212 mg.) was dissolved in a suspension of 2-methyl-2,3-methylene-6-aminopenam-3-carboxylic acid (428 mg.) in water (4 ml.). To a solution was added N-ethoxycarbonylphthalimide (440 mg.) all at once, and then stirred at room temprature for 2 hours. The resultant mixture was washed with methylene chloride. Methylene chloride (20 ml.) was added to the mixture, and then the solution was acidified with ¼N-hydrochloric acid (16 ml.) and extracted. The extract was washed with water, dried over magnesium sulfate and then the solvent removed under reduced pressure to give amorphous product. The product was dissolved in methanol (8 ml.). To the solution was added an aqueous solution of N,N-dibenzylethylenediamine acetate (220 mg.) in water (4 ml.) to give colorless crystals of N,N-dibenzylethylenediamine salt (280 mg.) of 2-methyl-2,3-methylene-6-phthalimidopenam-3-carboxylic acid, mp 181° to 182°C (dec.).

EXAMPLE 15

Triethylamine (1.4 g.) was added to a suspension of 2,2,2-trichloroethyl 2-methyl-2,3-methylene-6-aminopenam-3-carboxylate-1-β-oxide p-toluenesulfonate (3.48 g.) in dried methylene chloride (40 ml.) under cooling at −10°C. To the solution was dropwise added phenylthiocarbonylchloride (1.4 g.) and the reaction mixture was stirred for 2 hours. After the reaction, the resultant mixture was washed with 2% hydrochloric acid, a saturated aqueous solution of sodium bicarbonate and saturated aqueous solution of sodium chloride in turn, and then dried over magnesium sulfate. The solvent was removed under reduced pressure and the residue dissolved in a small amount of ethanol under heating. After allowing to stand at room temperature, crystals precipitated were filtered to give product of 2,2,2-trichloroethyl 2-methyl-2,3-methylene-6-(phenylthio)-carbonylaminopenam-3-carboxylate-1-$\beta$-oxide (2.8 g.), mp. 171.5° to 172.5°C.

EXAMPLE 16

In a suspension of 2,2,2-trichloroethyl 2-methyl-2,3-methylene-6-aminopenam-3-carboxylate-1-$\beta$-oxide p-toluenesulfate (3.2 g.) in dried methylene chloride (30 ml.) was dissolved triethylamine (1.3 g.) under ice-cooling. To the mixture was added 4-acetamidobenzenesulfonyl chloride (1.4 g.), and the mixture was stirred for 6 hours at the same temperature and then the resultant mixture was stirred at room temperature over night. After the reaction, the reaction mixture was washed with 2% hydrochloric acid, an aqueous solution of sodium bicarbonate and a saturated aqueous solution of sodium chloride in turn, dried and then the solvent removed. The residue was crystallized by adding a small amount of ethanol to give 2,2,2-trichloroethyl 2-methyl-2,3-methylene-6-(4-acetamidobenzenesulfonamido)penam-3-carboxylate-1-$\beta$-oxide (2.2 g.), mp. 149° to 153°C.

EXAMPLE 17

To solution of benzyloxycarbonyl chloride (2.55 g.) in dried methylene chloride (20 ml.) was dropwise added a solution of 2,2,2-trichloroethyl 2-methyl-2,3-methylene-6-aminopenam-3-carboxylate-1-$\beta$-oxide p-toluenesulfonate (5.3 g.) and triethylamine (2.8 g.) in absolute methylene chloride (20 ml.) under cooling at $-15°C$ and then the mixed solution was stirred at the same temperature for 3 hours. The methylene chloride layer was washed with 5% hydrochloric acid, water, 5% aqueous solution of sodium bicarbonate and water in turn and dried. The solvent was removed under reduced pressure and the oily residue dissolved in ether. The insoluble was filtered off and the filtrate concentrated to give oily 2,2,2-trichloroethyl 2-methyl-2,3-methylene-6-benzyloxycarboxamidopenam-3-carboxylate-1-$\beta$-oxide (4 g.)
Infrared Absorption Spectrum (Liquid film): 3375, 1797, 1745, 1723 cm$^{-1}$

EXAMPLE 18

To a solution of 2,2,2-trichloroethyl 2-methyl-2,3-methylene-6-aminopenam-3-carboxylate-1-$\beta$-oxide p-toluenesulfonate (7.95 g.) and triethylamine (4.1 g.) in dried methylene chloride (150 ml.) was added a solution of 3-chlorophenylacetyl chloride (4.23 g.) in methylene chloride (15 ml.) under cooling at $-15°C$ and stirred at the same temperature for 2 hours. After the reaction, the resultant mixture was washed with 5% the hydrochloric acid, water, 5% aqueous solution of sodium bicarbonate and water in turn, and then dried. After removing the solvent, the oily residue was dissolved in ether. The solution was left to give crystals of 2,2,2-trichloroethyl 2-methyl-2,3-methylene-6-[2-(3-chlorophenyl)acetamido]penam-3-carboxylate-1-$\beta$-oxide (6.7 g.), mp 144° to 147°C (dec.).

EXAMPLE 19

Triethylamine (6.5 g.) was dissolved in a suspension of 2,2,2-trichloroethyl 2-methyl-2,3-methylene-6-aminopenam-3-carboxylate-1-$\beta$-oxide p-toluenesulfonate (16 g.) in dried methylene chloride (150 ml.) under-cooling at $-10°$ to $-15°C$. To the solution was dropwise added a solution of (1,2,5-thiadiazol-3-yl)acetyl chloride (5.9 g.) in dried methylene chloride (25 ml.) and stirred as same temperature fpr 3 hours. The resultant mixture was washed with 2% hydrochloric acid, a saturated aqueous solution of sodium bicarbonate and a saturated aqueous solution of sodium chloride in turn, and then dried over magnesium sulfate. After removing the solvent, the volatile component was removed under highly reduced pressure to give powder of 2,2,2-trichloroethyl 2-methyl-2,3-methylene-6-[2-(1,2,5-thiadiazol-3-yl)acetamido]penam-3-carboxylate-1-$\beta$-oxide (14.0 g.), mp 145° to 148°C (dec.).

EXAMPLE 20

To a mixture of toluenesulfonate (8.10 g.) of 2,2,2-trichloroethyl 2-methyl-2,3-methylene-6-aminopenam-3-carboxylate-1-$\beta$-oxide in methylene chloride (120 ml.) was added triethylamine (1.55 g.) under cooling at $-10°$ to $-15°C$ and the mixture was dissolved with stirring. To the solution was added a solution of 2-sulfophenylacetic acid anhydride (7.28 g.) with ethyl chlorocarbonate in methylene chloride (30 ml.) under cooling at $-10°$ to $-15°C$. The mixture was stirred at the same temperature for an hour and at room temperature for 3 hours. After the resultant mixture was concentrated under reduced pressure, the residue was dissolved in water. To the aqueous solution was added ethyl acetate (10 ml.) and acidified with 10% aqueous hydrochloric acid (pH 3 to 4). After salting-out with a saturated aqueous solution of sodium chloride, the precipitate was filtered off, washed with cold water and then dried over phosphorus pentoxide. The ethylacetate layer was separated from the filtrate, washed with a saturated aqueous solution of sodium chloride and dried. The precipitates were combined together to give 2,2,2-trichloroethyl 2-methyl-2,3-methylene-6-[2-sulfophenylacetamido]-penam-3-carboxylate-1-oxide. '(7.63 g.) mp. 235° to 240°C (dec.).

The following compounds were obtained by using the same procedures as those of the Example 1 to 20.
1. 2,2,2-trichloroethyl 2-methyl-2,3-methylene-6-(2-phenlacetamido)penam-3-carboxylate-1-$\beta$-oxide, mp. 148° to 148.5°C.
2. 2,2,2-trichloroethyl 2-methyl-2,3-methylene-6-(2-phenlacetamido)-penam-3-carboxylate-1-$\beta$-oxide, mp. 142° to 143°C (dec.).
3. 2,2,2-trichloroethyl 2-methyl-2,3-methylene-6-(2-phenlacetamido)-penam-3-carboxylate, mp. 140° to 143°C.
4. 2,2,2-trichloroethyl 2-methyl-2,3-methylene-6-[2-(1H-tetrazol-1-yl)acetamido]-penam-3-carboxylate, mp. 133° to 137°C.
5. 2,2,2-trichloroethyl 2-methyl-2,3-methylene-6-[2-(2-thienyl)acetamido]-penam-3-carboxylate, mp. 144° to 145°C.
6. 2,2,2-trichloroethyl 2-methyl-2,3-methylene-6-(3-phenylureido)-penam-3-carboxylate, mp. 153° to 155°C.
7. 2,2,2-trichloroethyl 2-methyl-2,3-methylene-6-[2-phenyl-2(2-chlorophenoxy)acetamido]penam-3-carboxylate, oil.
8. 2,2,2-trichloroethyl 2-methyl-2,3-methylene-6-(2-phenyl-2-formyloxyacetamido)penam-penam-3-carboxylate, oil.

9. 2,2,2-trichloroethyl 2-methyl-2,3-methylene-6-[2-(1,3,4-thiadiazol-2-ylthio)acetamido] penam-3-carboxylate, oil.
10. 2,2,2-trichloroethyl 2-methyl-2,3-methylene-6-[2-(5-chloro-1H-benzotriazol-1-yl)acetamido]penam-3-carboxylate, mp. 164° to 166°C.
11. 2,2,2-trichloroethyl 2-methyl-2,3-methylene-6-(methylthioacetamido)-penam-3-carboxylate, oil.
12. 2,2,2-trichloroethyl 2-methyl-2,3-methylene-6-(1-chclopropylethoxy)-carbonylaminopena-3-carboxylate, oil.
13. 2,2,2-trichloroethyl 2-methyl-2,3-methylene-6-[N-(1-cyclopropylethoxy)carbonylphenylglycyl] aminopenam-3-carboxylate, amorphous.
14. 2,2,2-trichloroethyl 2-methyl-2,3-methylene-6-[3-(2-chlorophenyl)-5-methylisoxazol-4-carbonamido]penam-3-carboxylate, foam.
15. 2,2,2-trichloroethyl 2-methyl-2,3-methylene-6-phenylglyoxylamido-penam-3-carboxylate, mp. 132° to 133°C.
16. 2,2,2-trichloroethyl 2-methyl-2,3-methylene-6-(phenylthio)-carbonylaminopenam-3-carboxylate, mp. 121°C.
17. 2,2,2-trichloroethyl 2-methyl-2,3-methylene-6-(4-acetamidobenzenesulfonamido)penam-3-carboxylate, mp. 193° to 198°C.
18. 2-methyl-2,3-methylene-6-(2-phenylacetamido)penam-3-carboxylic acid, mp. 112° to 118°C (dec.).
19. 2-methyl-2,3-methylene-6-[2-(1H-tetrazol-1-yl)acetamido]penam-3-carboxylic acid, mp. 167° to 170°C (dec.).
20. 2-methyl-2,3-methylene-6-[2-(2-thienyl)acetamido]penam-3-carboxylic acid, mp. 106° to 108°C (dec.)
21. 2-methyl-2,3-methylene-6-(3-phenylureido)penam-3-carboxylic acid, mp. 108° to 110°C (dec.)
22. N,N'-dibenzylethylenediamine salt of 2-methyl-2,3-methylene-6-[2-phenyl-2-(2-chlorophenoxy)acetamido]penam-3-carboxylic acid, mp. 107° to 110°C (dec.)
23. 2-methyl-2,3-methylene-6-(2-phenyl-2-forymyloxyacetamido)penam-3-carboxylic acid, oil.
24. Sodium salt of 2-methyl-2,3-methylene-6-[2-(1,3,4-thiadiazol-2-ylthio)acetamido]penam-3-carboxylic acid, mp. 171° to 177°C (dec.)
25. Sodium salt of 2-methyl-2,3-methylene-6-(2-methylthioacetamido)penam-3-carboxylic acid, mp. 178° to 181°C (dec.).
26. N,N'-dibenzylethylenediamine salt of 2-methyl-2,3-methylene-6-(1-cyclopropylethoxy)carbonylaminopenam-3-carboxylic acid, mp. 148° to 149.5°C (dec.).
27. 2-methyl-2,3-methylene-6-[N-(1-cyclopropylethoxy)aminopenam]-3-carboxylic acid, amorphous.
28. N,N'-dibenzylethylnediamine salt of 2-methyl-2,3-methylene-6-[3-(2-chlorophenyl)-5-methylisoxazol-4-carbonylamido]penam-3-carboxylic acid, mp. 97° to 100°C (dec.).
29. Sodium salt of 2-methyl-2,3-methylene-6-(2-hydroxy-2-phenylacetamido)penam-3-carboxylic acid, mp. 180° to 190°C (dec.).
30. 2-methyl-2,3-methylene-6-(2-phenyl-2-semicarbazonoacetamido)penam-3-carboxylic acid, mp. 198° to 199°C (dec.).
31. 2-methyl-2,3-methylene-6-(phenylthio)carbonylaminopenam-3-carboxylic acid, pm. 116° to 119°C.
32. 2-methyl-2,3-methylene-6-(4-acetamidobenzenesulfonamido)penam-3-carboxylic acid, mp. 230°C (dec.).
33. 2-methyl-2,3-methylene-6-(2-phenylglycyl)aminopenam-3-carboxylic acid, mp. 200° to 202°C (dec.).
34. 2,2,2-trichloroethyl 2-methyl-2,3-methylene-6-(2-phenyl-2-semicarbazonoacetamido)-penam-3-carboxylate, mp. 198° to 199°C (dec.).

Reaction of:

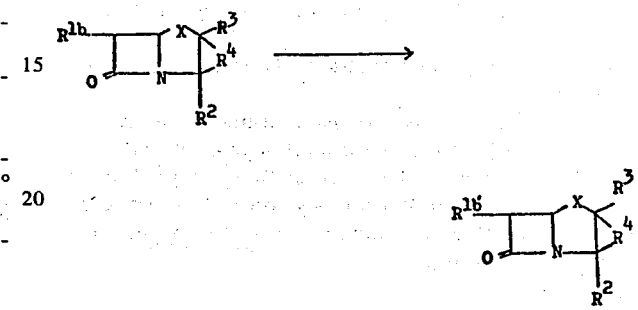

EXAMPLE 1

To a solution of 2,2,2-trichloroethyl 2-methyl-2,3-methylene-6-(2-phenylacetamido)penam-3-carboxylate (1.2 g.) in benzene (30 ml.) were added pyridine (0.36 g.) and phosphorus pentachloride (0.9 g.) under stirring and cooling at 10°C, and the mixture was stirred for 2 hours at room temperature. The solution was cooled at 10°C and absolute methanol (3 ml.) was added to the solution, after which the mixture was stirred for 2 hours at room temperature. Dimethylaniline (2.35 g.) and a solution of (2-thienyl)acetyl chloride (0.42 g.) in anhydrous benzene (5 ml.) were dropwise added to the solution under stirring and cooling at −5°C, and the mixture was stirred for 30 minutes at the same temperature and 1.5 hours at room temperature. The reaction mixture was washed with 5% hydrochloric acid, water, 5% sodium bicarbonate aqueous solution and water in turn and then dried. After drying, the solvent was removed and the residue oil was purified by column chromatography on silica gel (20 g.) using chloroform as developing solvent. The eluate was separated into each 50 ml. fraction and the 12th to 14th fractions were concentrated. The residue was crystallized from ether to give crystals of 2,2,2-trichloroethyl 2-methyl-2,3-methylene-6-[2-(2-thienyl)acetamido]penam-3-carboxylate (105 mg.), mp 144° to 145°C (dec.).

Reaction of:

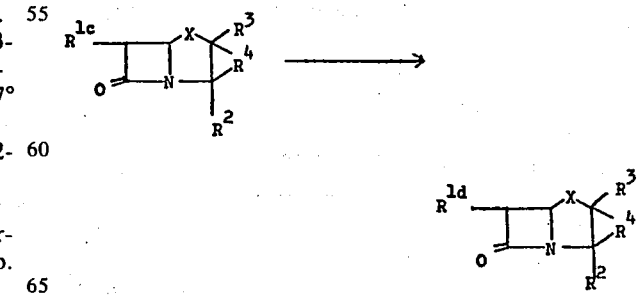

EXAMPLE 1

A solution of 2-methyl-2,3-methylene-6-[N-(1-cyclopropylethoxy) carbonyl-2-phenylglycyl]aminopenam- 3-carboxylic acid (1.88 g.) in formic acid (10 ml.) was stirred for 1 hour at room temperature and the solvent was distilled off under reduced pressure at room temperature. The residue was pulverized by adding ether and fitered. The powder was added to a mixture of acetonitrile (10 ml.) and water (1 ml.) and precipitated crystals were collected by filtration, washed with acetonitrile and dried to give 2-methyl-2,3-methylene-6-(2-phenylglycyl)aminopenam-3-carboxylic acid (0.89 g.), mp 200° to 202°C (dec.).

Analysis for $C_{16}H_{17}N_3O_4S1/2H_2O$: Calc'd: C 54.01, H 5.08, N 11.80, S 9.01; Found: C 54.09, H 4.80, N 11.46, S 9.24

Infrared Absorption Spectrum (Nujol): 3350, 1780, 1694, 1520 cm$^{-1}$

Similar result was obtained using 2-methyl-2,3-methylene-6-[N-(tert.-butoxycarbonyl)-2-phenylglycyl]-aminopenam-3-carboxylic acid instead of 2-methyl-2,3-methlene-6-[N-(1-cyclopropylethoxy)carbonyl-2-phenylglycyl]-aminopenam-3-carboxylic acid in the above example.

Reaction of:

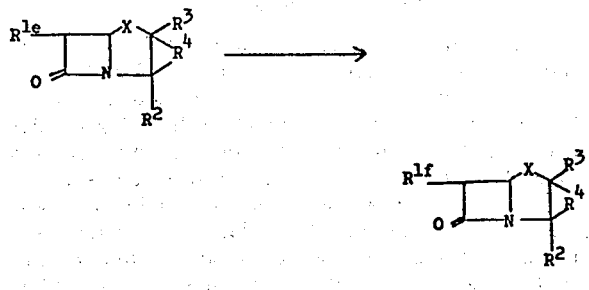

EXAMPLE 1

To a solution of 2-methyl-2,3-methylene-6-(2-phenyl-2-formyloxyacetamido)penam-3-carboxylic acid (1.1 g.) in methanol (10 ml.) and water (7 ml.) was added dropwise 1N-potassium hydroxide aqueous solution adjusting to pH 7 to 8, and the mixture was stirred for 10 minutes at room temperature. After the reaction was completed, methanol was distilled off from the reaction mixture under reduced pressure. The residual solution was acidified by adding 1N-hydrochloric acid and extracted with ethyl acetate. The solvent was distilled off from the extract under reduced pressure and the residue was pulverized by n-hexane to give 2-methyl-2,3-methylene-6-(2-phenyl-2-hydroxyacetamido)penam-3-carboxylic acid (0.4 g.).

Infrared Absorption Spectrum (Film): 1785, 1720, 1660 cm$^{-1}$

Reaction of:

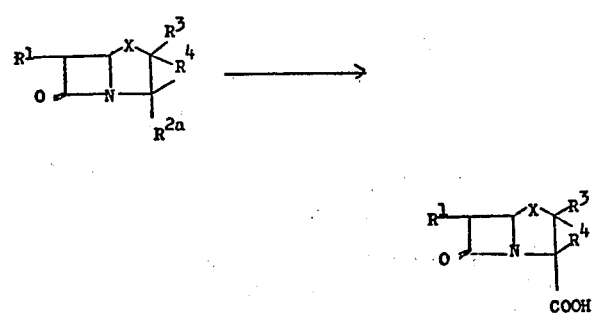

EXAMPLE 1

To a solution of 2,2,2-trichloroethyl 2-methyl-2,3-methylene-6-(2-phenylacetamido)penam-3-carboxylate (517 mg.) in a mixture of dimethylformamide (3 ml.) and acetic acid (1 ml.) was added zinc powder (0.7 g.) under ice-cooling. After stirring for 1 hour at the same temperature, zinc powder was filtered off and washed twice with dimethylformamide (2 ml.). The filtrate was combined with the washings and the combined solution was poured into a mixed cooled solution of ethyl acetate and water, extracted with ethyl acetate, after which the extract was washed with water and dried over magnesium sulfate. Crystalline material (390 mg.) obtained by distilling off the solvent under reduced pressure was washed with ether and dried to give colorless crystals of 2-methyl-2,3-methylene-6-(2-phenylacetamido)penam-3-carboxylic acid (310 mg.) mp 112° to 118°C (dec.).

Infrared Absorption Spectrum (Nujol): 3300, 1763, 1722, 1665 cm$^{-1}$

EXAMPLE 2

To a solution of 2,2,2-trichloroethyl 2-methyl-2,3-methylene-6-[2-(1H-tetrazol-1-yl)acetamido]penam-3-carboxylate (0.91 g.) in a mixture of dimethylformamide (5 ml.) and acetic acid (1.5 ml.) was added zinc powder (1.2 g.) under ice-cooling, and the mixture was stirred for 1 hour. After the reaction, the reaction mixture was poured into a mixture of 2% hydrochloric acid saturated with sodium chloride (30 ml.) and ethyl acetate (50 ml.), extracted and the aqueous layer was further extracted with ethyl acetate (10 ml.). The combined ethyl acetate layer was washed with a saturated sodium chloride aqueous solution and dried over magnesium sulfate. After drying, residue obtained by distilling off the solvent under reduced pressure was crystalized by adding a small amount of ethyl acetate and the crystals were collected by filtration to give 2-methyl-2,3-methylene-6-[2-(1H-tetrazol-1-yl)acetamido]penam-3-carboxylic acid (0.45 g.), mp 167° to 170°C (dec.).

Infrared Absorption Spectrum (Nujol): 3250, 1775, 1740, 1700 cm$^{-1}$

EXAMPLE 3

To a solution of 2,2,2-trichloroethyl 2-methyl-2,3-methylene-6-[2-(2-thienyl)acetamido]penam-3-carboxylate (1.4 g.) in a mixture of dimethylformamide (7.5 ml.) and acetic acid (1.75 ml.) was added zinc powder (1.8 g.) unde ice cooling, and the mixture was stirred for 1 hour. After the reaction, the reaction mixture was post-treated in the similar manner as described in Example 1 to give 2-methyl-2,3-methylene-6-[2-(2-thienyl)acetamido]penam-3-carboxylic acid (0.8 g.), mp 106° to 108°C (dec.) Infrared Absorption Spectrum (Nujol): 3350, 1765, 1720 cm$^{-1}$

EXAMPLE 4

To a solution of 2,2,2-trichloroethyl 2-methyl-2,3-methylene-6-(3-phenylureido)penam-3-carboxylate (1.12 g.) in dimethylformamide (7.5 ml.) were added acetic acid (2.3 ml.) and then zinc powder (1.8 g.) under ice-cooling, and the mixture was stirred for 1 hour. After the reaction, the reaction mixture was post-treated in the similar manner as described in Example 1 and residue obtained by distilling off ethyl acetate was crystallized by adding a small amount of acetonitrile to give colorless crystals of 2-methyl-2,3-methylene-6-(3-phenylureido)penam-3-carboxylic acid (0.72 g.), mp 108° to 110°C.
Infrared Absorption Spectrum (Nujol): 3350, 3300, 1765, 1710, 1665 cm$^{-1}$

EXAMPLE 5

To a solution of 2,2,2-trichloroethyl 2-methyl-2,3-methylene-6-[2-phenyl-2-(2-chlorophenoxy)acetamido]penam-3-carboxylate (1.18 g.) in a mixture of dimethylformamide (5 ml.) and acetic acid (1.5 ml.) was added zinc powder (1.2 g.) under ice-cooling, and the mixture was stirred for 1.5 hours. After the reaction, the residue (0.65 g.) obtained by post-treating the reaction mixture in the similar manner as described in Example 1 was dissolved in methanol (2 ml.) and a solution of N,N'-dibenzylethylenediamine diacetate (0.20 g.) in water (10 ml.) was added to the solution. Crystals obtained in this manner were dissolved in methanol and subjected to reprecipitation with water to give N,N'-dibenzylethylenediamine salt of 2-methyl-2,3-methylene-6-[2-phenyl-2-(2-chlorophenoxy)acetamido]penam-3-carboxylic acid (0.55 g.), mp 107° to 110°C (dec.)
Infrared Absorption Spectrum (Nujol): 1785, 1690 cm$^{-1}$

EXAMPLE 6

To a solution of 2,2,2-trichloroethyl 2-methyl-2,3-methylene-6-(2-phenyl-2-formyloxyacetamido)penam-3-carboxylate (1.52 g.) in dimethylformamide (7.5 ml.) were added acetic acid (2.3 ml.) and zinc powder (1.8 g.) under ice-cooling, and the mixture was stirred for 1 hour. After the reaction, the reaction mixture was post-treated in the similar manner as described in Example 1 to the distillation of ethyl acetate to give oily 2-methyl-2,3-methylene-6-(2-phenyl-2-formyloxyacetamido)penam-3-carboxylic acid (1.1 g.).
Infrared Absorption Spectrum (Film): 1785, 1720 cm$^{-1}$

EXAMPLE 7

To a solution of 2,2,2-trichloroethyl 2-methyl-2,3-methylene-6-[2-(1,3,4-thiadiazol-2-ylthio)acetamido]penam-3-carboxylate (2.5 g.) in a mixture of dimethylformamide (12.5 ml.) and acetic acid (3.8 ml.) was added zinc powder (3 g.) under ice-cooling, and the mixture was stirred for 1 hour. After the reaction, the reaction mixture was post-treated in the similar manner as described in Example 1 to the distillation of ethyl acetate and the obtained oily material was led to its sodium salt by a conventional method to give sodium 2-methyl-2,3-methylene-6-[2-(1,3,4-thiadiazol-2-ylthio)acetamido]penam-3-carboxylate (0.6 g.), mp 171° to 177°C (dec.).
Infrared Absorption Spectrum (Nujol): 1790, 1670, 1590 cm$^{-1}$

EXAMPLE 8

To a solution of 2,2,2-trichloroethyl 2-methyl-2,3-methylene-6-(2-methylthioacetamido)penam-3-carboxylate (0.9 g.) in a mixture of dimethylformamide (5 ml.) and acetic acid (1.5 ml.) was added zinc powder (1.2 g.) under ice-cooling, and the mixture was stirred for 1 hour. After the reaction, zinc powder was filtered and the filtrate was poured into a mixture of ethyl acetate (20 ml.) and ice-water (20 ml.) containing 10% hydrochloric acid (2 ml.) The ethyl acetate layer was separated and the aqueous layer was further extracted with ethyl acetate (10 ml.). The combined ethyl acetate layer was washed with water and a saturated sodium chloride aqueous solution in turn and then dried over magnesium sulfate. After drying, the residue obtained by removing the solvent was led to its sodium salt by a conventional method to give sodium 2-methyl-2,3-methylene-6-(2-methylthioacetamido)-penam-carboxylate (0.63 g.), mp 178° to 181°C (dec.).
Infrared Absorption Spectrum (KBr tablet): 1775, 1665, 1610 cm$^{-1}$

EXAMPLE 9

To a solution of 2,2,2-trichloroethyl 2-methyl-2,3-methylene-6-(1-cyclopropylethoxy)carbonylaminopenam-3-carboxylate (1.78 g.) in dimethylformamide (10 ml.) were added acetic acid (3 ml.) and zinc powder (2.4 g.), and the mixture was stirred for 1 hour. The zinc powder was filtered, washed with dimethylformamide and the filtrate and the washings were poured into a mixture of ethyl acetate and ice-water. The solution was adjusted to about pH 2 with 10% hydrochloric acid and extracted. The extract was washed with water, extracted with a sodium bicarbonate aqueous solution to pH 7 and this aqueous solution was acidified with 10% hydrochloric acid and then extracted with ethyl acetate. The extract was washed with water, dried over magnesium sulfate and the solvent was remove under reduced pressure to give amorphous carboxylic acid (840 mg.). The acid was dissolved in methanol and a N,N'-dibenzylethylenediamine diacetate aqueous solution was added to the solution, after which the precipitates were collected by filtration and dried to give N,N'-dibensylethylenediamine salt of 2-methyl-2,3-methylene-6-(1-cyclopropylethoxy)-carbonylaminopenam-3-carboxylic acid, mp 148° to 149.5°C (dec.).
Infrared Absorption Spectrum (Nujol): 3210, 1770, 1715, 1605 cm$^{-1}$

EXAMPLE 10

2,2,2-Trichloroethyl 2-methyl-2,3-methylene-6-[N-(1-cyclopropylethoxy) carbonylphenylglycyl]aminopenam-3-carboxylate (3.66 g.) was treated in the similar manner as described in Example 9 and the reaction mixture was filtered. The filtrate was poured into a mixture of ethyl acetate and ice-cooled 2% hydrochloric acid and extracted and then the ethul acetate layer was separated. The extract was washed with a saturated sodium chloride aqueous solution, dried over magnesium sulfate and the solvent was removed to give amorphous 2-methyl-2,3-methylene-6-[N-(1-cyclopropylethoxy) carbonylphenylglycyl]aminopenam-3-carboxylic acid (3.04 g.).
Infrared Absorption Spectrum (Nujol): 3290, 1790, 1720, 1710, 1670 cm$^{-1}$

EXAMPLE 11

2,2,2-Trichloroethyl-2-methyl-2,3-methylene-6-[3-(2-chlorophenyl)-5-methylisoxazol-4-carboxamido]penam-3-carboxylate (2 g.) was treated in the similar manner as described in Example 10 to give 2-methyl-2,3-methylene-6-[3-(2-chlorophenyl)-5-methylisoxazol-4-carboxamido]penam-3-carboxylic acid (1.31 g.). This carboxylic acid was converted into its N,N'-dibenzylethylenediamine salt by using N,N'-dibenzylethylenediamine diacetate to give N,N'-dibenzylethylenediamine salt of 2-methyl-2,3-methylene-6-[3-(2-chlorophenyl)-5-methylisoxazol-4-carboxamido]penam-3-carboxylic acid, mp 97° to 100°C (dec.).
Infrared Absorption Spectrum (Nujol): 3400, 1785, 1670, 1603, 1510 cm$^{-1}$

EXAMPLE 12

To a solution of 2,2,2-trichloroethyl-2-methyl-2,3-methylene-6-phenylglyoxylamidopenam-3-carboxylate (1.44 g.) in dimethylformamide (10 ml.) were added acetic acid (2.3 ml.) and zinc powder (2.25 g.) under ice-cooling, and the mixture was stirred for 1 hour. After the reaction, zinc powder was filtered off and the filtrate was poured into a mixture of ethyl acetate and dilute hydrochloric acid. After the extraction, the extract was extracted with a sodium bicarbonate aqueous solution. The extract was acidified by adding hydrochloric acid, extracted with ethyl acetate and the extract was washed with water and then dried over magnesium sulfate. After drying, the solvent was distilled off under reduced pressure to give amorphous 2-methyl-2,3-methylene-6-phenylglyoxylamidopenam-3-carboxylic acid (790 mg.). This compound (346 mg.) was dissolved in acetone (1 ml.) and an acetone solution containing sodium 2-ethylhexanoate (138 mg.) was added to the solution. Ether was added to the solution and the precipitates were collected by filtration and washed with ether to give sodium 2-methyl-2,3-methylene-6-(2-hydroxy-2-phenylacetamido)-3-carboxylate (250 mg.), mp 180° to 190°C (dec.).
Infrared Absorption Spectrum (KBr tablet): 3400, 1770, 1670, 1605 cm$^{-1}$

EXAMPLE 13

To a solution of 2,2,2-trichloroethyl 2-methyl-2,3-methylene-6-(2-phenyl-2-carbamoylhydrazonoacetamido)penam-3-carboxylate (560 mg.) in dimethylformamide (3 ml.) were added acetic acid (0.8 ml.) and zinc powder (0.75 g.) under ice-cooling, and the mixture was stirred for 1.5 hours. Zinc powder was filtered off, washed with dimethylformamide and the filtrate and the washings were combined, after which the combined solution was poured into ice-water. The solution was adjusted to pH 2 with 10% hydrochloric acid and precipitated crystals were filtered, washed with ethyl acetate and dissolved in a sodium bicarbonated aqueous solution. Insoluble material was filtered off and the filtrate was acidified with 10% hydrochloric acid to give 2-methyl-2,3-methylene-6-(2-phenyl-2-carbamoylhydrazonoacetamido)penam-3-carboxylic acid (270 mg.), mp 198° to 199°C (dec.).
Infrared Absorption Spectrum (Nujol): 3260, 1763, 1710, 1692, 1650 cm$^{-1}$

EXAMPLE 14

Acetic acid (2 ml.) was added to a solution of 2,2,2-trichloroethyl 2-methyl-2,3-methylene-6-[1-(4-chlorophenyl)imino-1-acetylthiomethyl] aminopenam-3-carboxylate (1.05 g.) in dimethylformamide (5 ml.), and then zinc powder (2 g.) was added to the solution at −5° to −8°C, after which the mixture was stirred for a hours at the same temperature. After the reaction, zinc powder was filtered off and the filtrate was poured into ice cooled mixture of ethyl acetate and dilute hydrochloric acid and then extracted. The extract was washed with water, dried over magnesium sulfate and the solvent was distilled off under reduced pressure. The obtained amorphous compound (770 mg.) was crystallized by adding acetonitrile. The crystals were washed with acetonitrile and combined with crystals obtained from the washings to give 2-methyl-2,3-methylene-6-[1-(4-chlorophenyl)imino-1-acetylthiomethyl]aminopenam-3-carboxylic acid (510 mg.), mp 147° to 150°C (dec.).
Infrared Absorption Spectrum (Nujol): 3120, 1802, 1703, 1683 cm$^{-1}$

EXAMPLE 15

To a solution of 2,2,2-trichloroethyl 2-methyl-2,3-methylene-6-(phenylthio)carbonylaminopenam-3-carboxylate (1.04 g.) in a mixture of dimethylformamide (7 ml.) and acetic acid (2.2 ml.) was added zinc powder (1.8 g.) under ice-cooling, and the mixture was stirred for 1.5 hours. After the reaction, zinc powder was filtered off and the filtrate was poured into a mixture of ethyl acetate (30 ml.) and ice-water (30 ml.) containing 2% hydrochloric acid (2 ml.), extracted and then the aqueous layer was further extracted with ethyl acetate (10 ml.) The combined extract was washed with water and a saturated sodium chloride aqueous solution in turn, dried over magnesium sulfate and then the solvent was removed under reduced pressure. The obtained residue was crystallized by adding a small amount of acetonitrile to give 2-methyl-2,3-methylene-6-(phenylthio)carbonylaminopenam-3-carboxylic acid (0.43 g.), mp 116° to 119°C (dec.).
Analysis for $C_{15}H_{14}N_2O_4S_2$: Calc'd : C 51.42, H 4.03, N 7.73; Found : C 51.16, H 3.94, N 8.02

EXAMPLE 16

2,2,2-Trichloroethyl 2-methyl-2,3-methylene-6-(4-acetamidobenzenesulfonamido)penam-3-carboxylate (1.09 g.), acetic acid (1.5 ml.) and zinc powder (1.2 g.) were treated in the similar manner as described in Example 1 and the residue was crystallized using ethyl acetate to give 2-methyl-2,3-methylene-6-(4-acetamidobenzenesulfonamido)penam-3-carboxylic acid (0.5 g.), mp. 230°C (dec.).

EXAMPLE 17

To a solution of 2,2,2-trichloroethyl 2-methyl-2,3-methylene-6-[2-(5-chlorobenzotriazol-1-yl)acetamido]penam-3-carboxylate (1.04 g.) in a mixtue of dimethylformamide (5 ml.) and acetic acid (1.5 ml.) was added zinc powder (1.2 g.) under ice-cooling, and the mixture was stirred for 1.5 hours. After the reaction, zinc powder was filtered and the filtrate was poured into a mixture of ice-water (20 ml.) containing 10% hydrochloric acid (2 ml.) and ethyl acetate (20 ml.) and extracted. The ethyl acetate layer was washed with water and a saturated sodium chloride aqueous solution in turn and then dried over magnesium sulfate. The solvent was removed under reduced pressure and the residue was dissolved in a small amount of acetone and converted into its sodium salt by adding an acetone solution of sodium ethylhexanonate to give sodium 2-methyl-2,3-methylene-6-[2-(5-chlorobenzotriazol-1-yl)acetamido]-penam-3-carboxylate (0.43 g.), mp 230°C (dec.).

The following compounds were obtained by using the same procedures as those of the Examples 1 to 17.
1. N,N'-dibenzylethylenediamine salt of 2-methyl-2,3-methylene-6-phthalimidopenam-3-carboxylic acid, mp 181° to 182°C (dec.).
2. 2-Methyl-2,3-methylene-6-aminopenam-3-carboxylic acid, mp 200°C (dec.).

3. 2-Methyl-2,3-methylene-6-(2-phenylglycyl-)aminopenam-3-carboxylic acid, mp 200° to 202°C (dec.).

Reaction of:

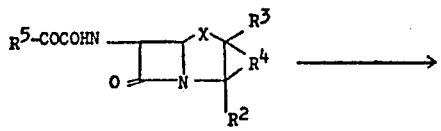

→

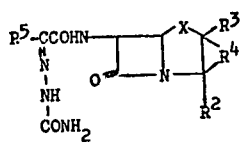

EXAMPLE 1

2,2,2-Trichloroethyl 2-methyl-2,3-methylene-6-phenylglyoxylamidopenam-3-carboxylate (477 mg.) and ethanol (10 ml.) were added to a solution of semicarbazide hydrochloride (112 mg.) and anhydrous sodium acetate (82 mg.) in water (2 ml.), and the mixture was refluxed for 1 hour. After the reaction was completed, precipitated crystals were collected by filtration, washed with water and dried to give colorless crystals of 2,2,2-trichloroethyl 2-methyl-2,3-methylene-6-(2-phenyl-2-semicarbazonoacetamido)penam-3-carboxylate (190 mg.), mp 200° to 201°C (dec.).
Infrared Absorption Spectrum (Nujol): 3450, 3250, 1770, 1745, 1680 cm$^{-1}$ Reaction of:

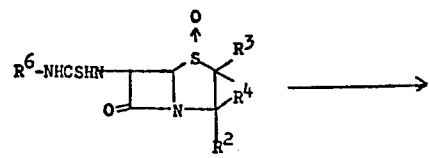

→

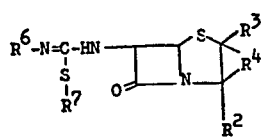

EXAMPLE 1

To a suspension of 2,2,2-trichloroethyl 2-methyl-2,3-methylene-6-[3-(4-chlorophenyl)thioureido] penam-3-carboxylate-1-oxide (1.36 g.) in a mixture of dimethylformamide (4 ml.) and acetonitrile (8 ml.) were added stannous chloride (3 g.) and acetyl chloride (3 ml.) under cooling at −10°C, and the mixture was stirred for 3 hours at the same temperature. After the reaction, the reaction mixture was poured into a mixture of ice-water and ethyl acetate and extracted with ethyl acetate. The extract was sufficiently washed with 5% hydrochloric acid and a sodium bicarbonate aqueous solution and then the insoluble substance was filtered off. The filtrate was further washed with water and dried over magnesium sulfate. After drying, the solvent was removed under reduced pressure to give amorphous compound (1.22 g.). This compound was purified by column chromatography on silica gel using chloroform as developing solvent to give amorphous 2,2,2-trichloroethyl 2-methyl-2,3-methylene-6-[1-(4-chlorophenyl)imio-1-acetylthiomethyl] amino-penam-3-carboxylate (1.19 g.).
Infrared Absorption Spectrum (CHCl$_3$): 3125, 1790, 1742, 1680 cm$^{-1}$

What we claim is:

1. A process for the preparation of

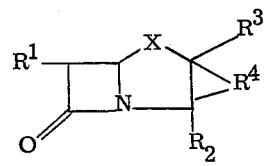

which comprises reacting

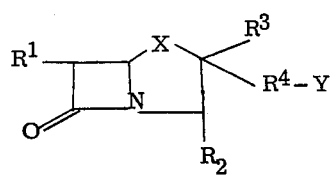

with a base, wherein Y is a residue of an acid obtained by omitting a hydrogen atom from an acid selected from the group consisting of halogen, methanesulfonyloxy, benzenesulfonyloxy, and toluene sulfonyloxy, wherein R$^1$ is amino (1-halophenylimino-1-lower alkanoylthiomethyl)amino or a conventional penicillin acylamino group and wherein R$^2$ is carboxy or a conventional penicillin protected carboxy, R$^3$ is lower alkyl, R$^4$ is lower alkylene and X is

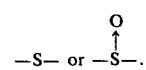

* * * * *